US008071380B2

(12) United States Patent
Cossu et al.

(10) Patent No.: US 8,071,380 B2
(45) Date of Patent: Dec. 6, 2011

(54) SKELETAL MUSCLE PERIANGIOBLASTS AND CARDIAC MESANGIOBLASTS, METHOD FOR ISOLATION AND USES THEREOF

(75) Inventors: Giulio Cossu, Milan (IT); Beatriz Galvez Gonzales, Milan (IT); Rossana Tonlorenzi, Milan (IT)

(73) Assignee: Fondazione Centro San Raffaele Del Monte Tabor, Milan (IT)

( * ) Notice: Subject to any disclaimer, the term of this patent is extended or adjusted under 35 U.S.C. 154(b) by 0 days.

(21) Appl. No.: 12/279,716

(22) PCT Filed: Feb. 15, 2007

(86) PCT No.: PCT/EP2007/001309

§ 371 (c)(1),
(2), (4) Date: Aug. 16, 2008

(87) PCT Pub. No.: WO2007/093412

PCT Pub. Date: Aug. 23, 2007

(65) Prior Publication Data

US 2009/0317909 A1    Dec. 24, 2009

Related U.S. Application Data

(60) Provisional application No. 60/774,882, filed on Feb. 16, 2006.

(51) Int. Cl.
*C12N 5/00* (2006.01)
*C12N 5/02* (2006.01)
(52) U.S. Cl. .................. 435/378; 435/325; 435/384
(58) Field of Classification Search .................. 435/325, 435/378, 384
See application file for complete search history.

(56) References Cited

U.S. PATENT DOCUMENTS

| | | | |
|---|---|---|---|
| 6,387,369 B1 | 5/2002 | Pittenger et al. | |
| 2003/0216332 A1 | 11/2003 | Chamberlain et al. | |
| 2005/0181502 A1 | 8/2005 | Furcht et al. | |
| 2006/0111290 A1 | 5/2006 | Itescu | |
| 2006/0239983 A1 | 10/2006 | Anversa | |
| 2006/0286544 A1 | 12/2006 | Mandal et al. | |

FOREIGN PATENT DOCUMENTS

| | | |
|---|---|---|
| WO | 1999/003973 | 1/1999 |
| WO | 1999049015 | 9/1999 |
| WO | 2001/094420 | 12/2001 |
| WO | 2002097066 | 12/2002 |
| WO | 2003006950 | 1/2003 |
| WO | 2003/024462 | 3/2003 |
| WO | 2003095631 | 11/2003 |
| WO | 2004019767 | 3/2004 |
| WO | 2005/012510 | 2/2005 |
| WO | 2006/011061 | 2/2006 |

OTHER PUBLICATIONS

Allegrucci et al., 2006, Human Reproduction Update, Vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Yu et al., 2006, American Journal of Pathology, vol. 168, No. 6, p. 1-6.*
Cotsarelis, G., 2006, The Journal of Clinical Investigation, vol. 116, No. 1, p. 19-22.*
International Search Report; PCT/EP2007/001309; published Nov. 22, 2007.
Bergers, et al, "The role of pericytes in blood-vessel formation and maintenance," Neuro-Oncology, Jul. 2005, pp. 452-464, Society for Neuro-Oncology, San Francisco, CA.
Dellavalle, et al., "Pericytes of human skeletal muscle are myogenic precursors distinct from satellite cells," Nature Cell Biology, Mar. 2007, pp. 255-267, vol. 9, No. 3.
Guttinger, et al., "Allogeneic mesoangioblasts give rise to alpha-sarcoglycan expressing fibers when transplanted into dystrophic mice," Science Direct, Aug. 2006, pp. 3872-3879, Experimental Cell Research 312, Elsevier, Inc.
Morosetti, et al., "MyoD expression restores defective myogenic differentiation of human mesoangioblasts from inclusion-body myositis," PNAS, Nov. 7, 2006, pp. 16995-17000, vol. 103, No. 45, The National Academy of Sciences of the USA.
Sampaolesi, et al., "Cell Therapy of Alpha-Sarcoglycan Null Dystrophic Mice Through Intra-Arterial Delivery of Mesoangioblasts," Science, Jul. 25, 2003, pp. 487-492, vol. 301, www.sciencemag.org.
Sampaolesi, et al., "Mesoangioblast stem cells ameliorate muscle function in dystrophic dogs," Nature, Nov. 15, 2006, pp. 1-6, www.nature.com, Nature Publishing Group.
Reyes, et al., "Purification and ex vivo expansion of postnatal human marrow mesodermal progenitor cells," Blood, Nov. 1, 2001, pp. 2615-2625, vol. 98, No. 9, W.B. Saunders Company, Orlando, FL, US.
Minasi, et al., "The meso-angioblast: a multipotent, self-renewing cell that originates from the dorsal aorta and differentiates into most mesodermal tissues," Development 129, Jun. 2002, pp. 2772-2783, The Company of Biologists Limited 2002, Cambridge, GB.
Yin, et al., "AC133, a Novel Marker for Human Hematopoietic Stem and Progenitor Cells," Blood, Dec. 15, 1997, pp. 5002-5012, vol. 90, No. 12, W.B. Saunders Company, Orlando, FL, US. Cossu, et al. "Mesoangioblasts, vessel associated stem cells, repair skeletal muscle in animal models of muscular dystrophies," Experimental Hematology, Jul. 2005, pp. 39-72, New York, NY, US, and ABSTRACTS of Oral Presentations, 34th Annual Meeting, International-Society-for-Experimental Hematology, Abstract No. 8, Jul. 30-Aug. 2, 2005, Glasgow, Scotland.
Messina, et al., "Isolation and Expansion of Adult Cardiac Stem Cells From Human and Murine Heart," Research, Journal of the American Heart Association, Oct. 29, 2004, pp. 911-921, The American Heart Associate, Dallas, Texas and Supplemental Material, 22 pages downloaded from circres.ahajounals.org at Fondazione Centro San Raffaele on Dec. 20, 2010.
Condorelli, et al., "Cardiomyocytes induce endothelial cells to transdifferentiate into cardiac muscle: Implications for myocardium regeneration," PNAS, Sep. 11, 2001, pp. 10733-10738, vol. 98, No. 19.

(Continued)

*Primary Examiner* — Shin-Lin Chen
(74) *Attorney, Agent, or Firm* — Lucas & Mercanti, LLP

(57) ABSTRACT

The present invention discloses the isolation and characterization of cells isolated either from adult skeletal muscle or from adult cardiac muscle. These cells are used for the treatment of muscular disorders including muscular dystrophy and cardiopathics, respectively.

7 Claims, 16 Drawing Sheets

OTHER PUBLICATIONS

Figure 2:
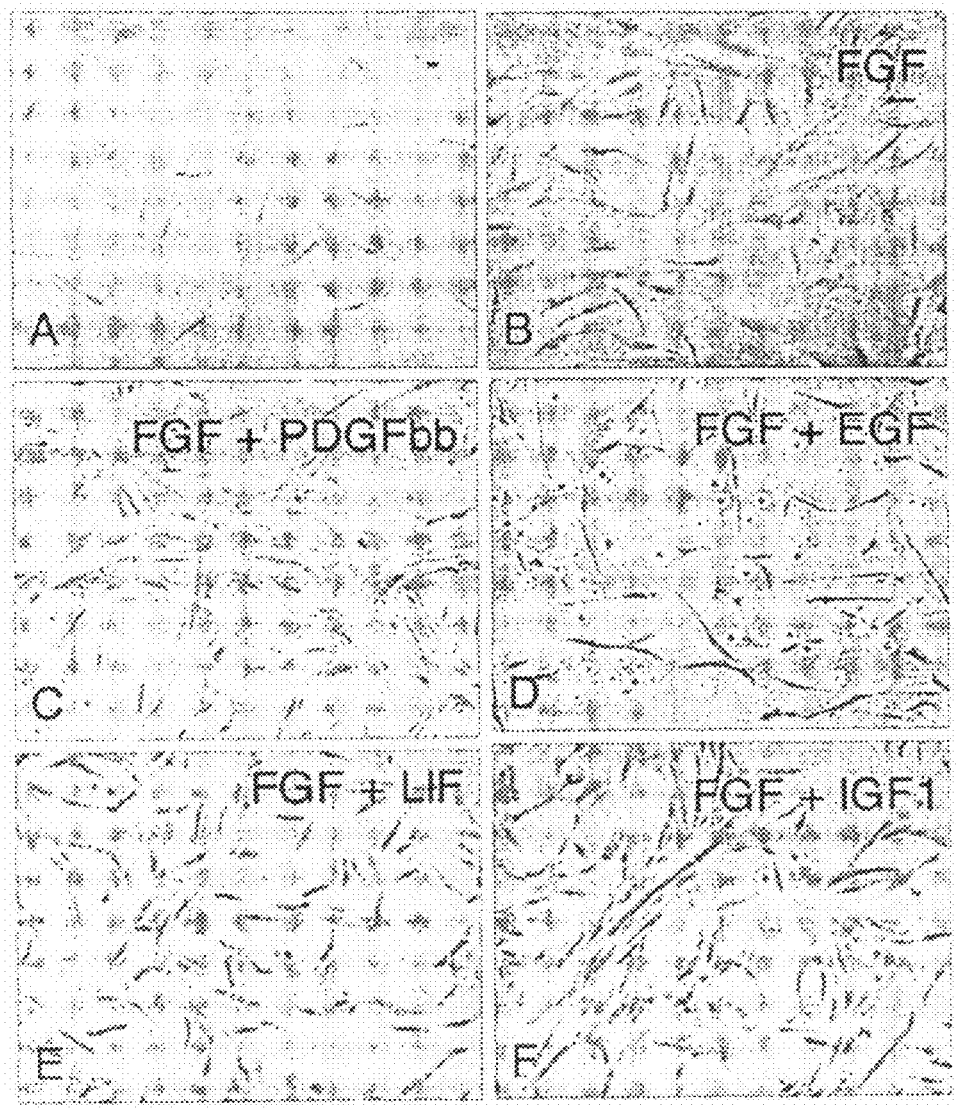

Dezawa, et al., "Bone Marrow Stromal Cells Generate Muscle Cells and Repair Muscle Degeneration," Science, Jul. 8, 2005, pp. 314-317, vol. 309, American Association for the Advancement of Science (AAAS), Washington, D.C.

Orlic, et al., "Bone Marrow Cells Regenerate Infarcted Myocardium," Nature, Apr. 5, 2001, pp. 701-705, vol. 410, Macmillan Magazine Ltd.

Kocher, et al., "Neovascularization of ischemic myocardium by human bone-marrow-derived angioblasts prevents cardiomyocyte apoptosis, reduces remodeling and improves cardiac function," Nature Medicine, Apr. 2001, pp. 430-436, vol. 7, No. 4, Nature Publishing Group.

Sciorati, et al, "Ex vivo treatment with nitric oxide increases mesoangioblast therapeutic efficacy in muscular dystrophy," Journal of Cell Science, Oct. 12, 2006, pp. 5114-5123, vol. 119, The Company of Biologists.

Galvez, et al., "Complete repair of dystrophic skeletal muscle by mesoangioblasts with enhanced migration ability," The Journal of Cell Biology, Jul. 17, 2006, pp. 231-243, vol. 174, No. 2, The Rockefeller University Press.

Brachvogel, et al., "Perivascular cells expressing annexin A5 define a novel mesenchymal stem cell-like population with the capacity to differentiate into multiple mesenchymal lineages," Development and disease, Mar. 22, 2005, pp. 2657-2668, vol. 132, The Company of Biologists.

Galli, et al., "Mesoangioblasts, Vessel-Associated Multipotent Stem Cells, Repair the Infarcted Heart by Multiple Cellular Mechanisms," Arterioscler Thromb Vasc Biol., Apr. 2005, pp. 1-6, The American Heart Association, Dallas, Texas.

Cossu, et al., "New Therapies for muscular dystrophy: cautious optimism," Trends in Molecular Medicine, Oct. 2004, pp. 516-520, vol. 10, No. 10.

\* cited by examiner

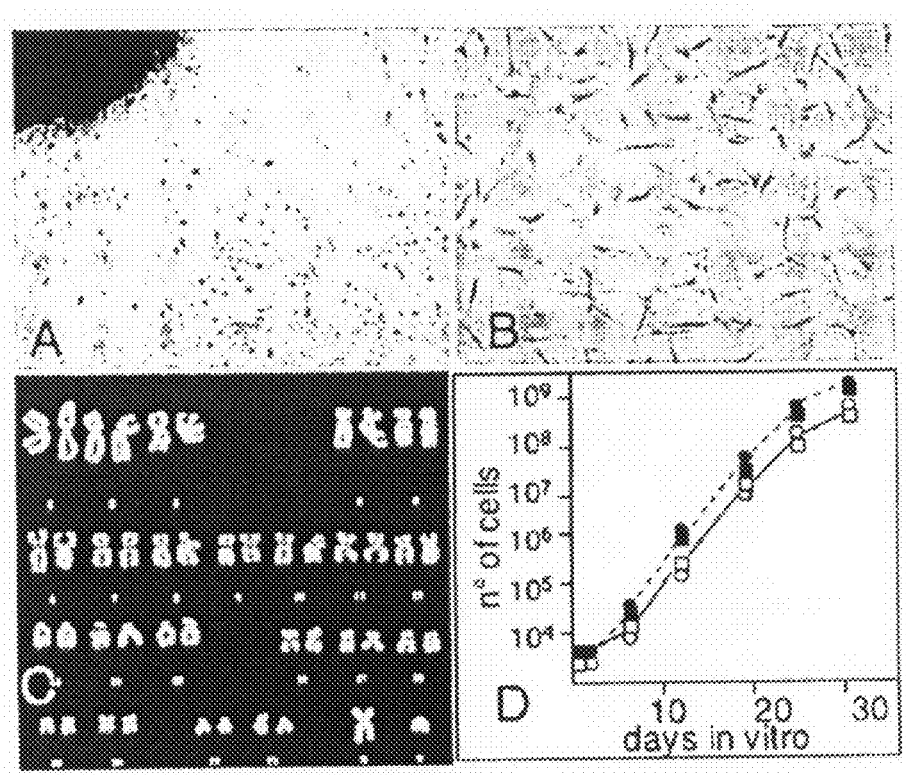
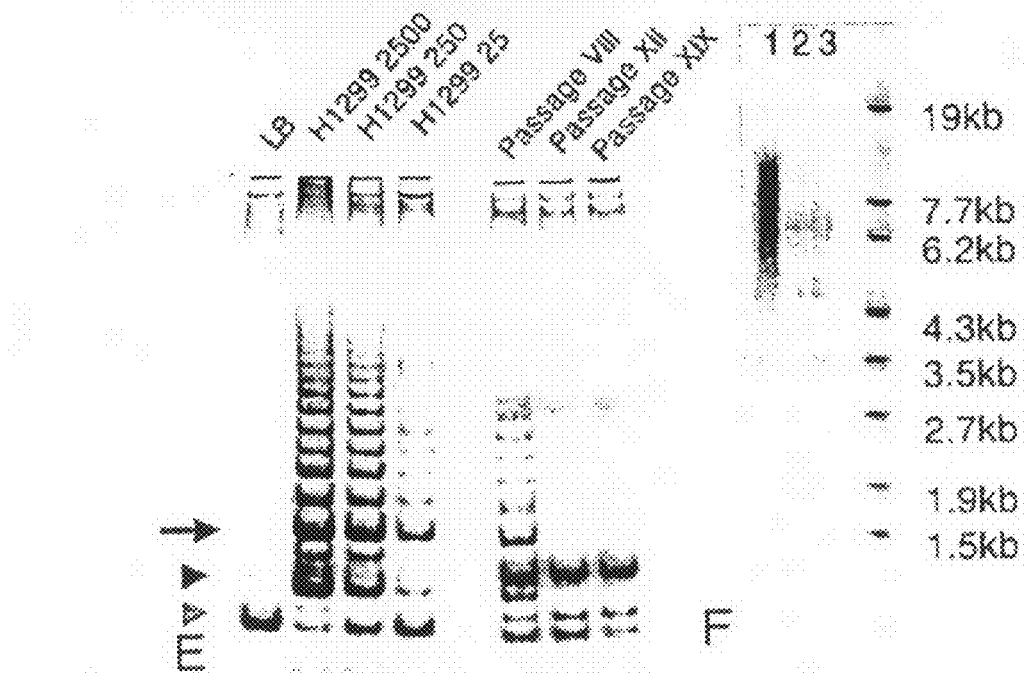
Fig. 1

Fig. 6

Increased in DMD

| ProbeSetID | Symbol | Gene | DMD3 | DMDA | MIX40Y | MIX78Y | CL9 | CLB | GeneName |
|---|---|---|---|---|---|---|---|---|---|
| 204470_at | CXCL1 | 2919 | | | 372.7 | | 119.7 | 196 | chemokine (C-X-C motif) ligand 1 (melanoma stimulating) |
| 205336_at | CXCL6 | 6372 | | | 490.3 | 175 | | 703 | chemokine (C-X-C motif) ligand 6 (granulocyte chemotactic) |
| 215336_at | IL8 | 3576 | | 719.9 | | | | 379.7 | interleukin 8 |
| 205207_at | IL6 | 3569 | | 534.4 | 107.1 | 119.2 | | 271.9 | interleukin 6 (interferon, beta 2) |
| 221477_s_at | MGC5618 | 79083 | | | 300.4 | 455 | 687.4 | 407.6 | hypothetical protein MGC5618 |
| 218854_s_at | GOS2 | 50486 | | | | 380.7 | 160.5 | 100.3 | putative lymphocyte G0/G1 switch gene |
| 209774_x_at | CXCL2 | 2920 | | 883.4 | | | | 139.6 | chemokine (C-X-C motif) ligand 2 |
| 204748_at | PTGS2 | 5743 | | 191.7 | | | | | prostaglandin-endoperoxide synthase 2 |
| 203267_s_at | SLC39A8 | 64116 | | 705.1 | 209.9 | 139.1 | 225.5 | 293.5 | solute carrier family 39 (zinc transporter), member 8 |
| 203719_at | ABCA8 | 10351 | | | 158.9 | 254.7 | 221.3 | 119.2 | ATP-binding cassette, sub-family A (ABC1), member 8 |
| 207850_at | CXCL3 | 2921 | | 487.3 | 175 | 121.3 | | 251.4 | chemokine (C-X-C motif) ligand 3 |
| 208731_at | TGFBR3 | 7049 | | | 272.4 | 389.7 | 193.9 | 160.4 | transforming growth factor, beta receptor III |
| 203407_at | HSD11B1 | 3290 | | | 137.7 | 752.4 | | 167.1 | hydroxysteroid (11-beta) dehydrogenase 1 |
| 202643_s_at | TNFAIP3 | 7128 | | 584.6 | 116.3 | 248.9 | | | tumor necrosis factor, alpha-induced protein 3 |
| 208358_s_at | FLRT2 | 23768 | | 645.7 | | 150.9 | | | fibronectin leucine rich transmembrane protein 2 |
| 202994_s_at | FBLN1 | 2192 | | 568.4 | 173.1 | | | 212 | fibulin 1 |

Decreased in DMD

| ProbeSetID | Symbol | Gene | DMD3 | DMDA | MIX40Y | MIX78Y | CL9 | CLB | GeneName |
|---|---|---|---|---|---|---|---|---|---|
| 202627_s_at | SERPNE1 | 5054 | 466.9 | 295.1 | 4089.6 | 3270.3 | | 6803.7 | serine (or cysteine) proteinase inhibitor |
| 206116_s_at | TPM1 | 7168 | 446.1 | 501.2 | 2258.7 | | 5154.8 | tropomyosin 1 (alpha) |
| 1553724_s_at | TAGLN | 6876 | | 397.5 | 1840.5 | 1055.9 | 477.6 | transgelin |
| 1558015_s_at | ACTR2 | 10097 | | 117.9 | 849.6 | 484.9 | | 579.8 | ARP2 actin-related protein 2 homolog (yeast) |
| 217816_s_at | ARPC4 | 10093 | | 106.3 | 802 | 511.3 | 651.6 | 493.5 | actin related protein 2/3 complex, subunit 4, 20kDa |
| 223832_at | WISP1 | 8840 | | | 765.7 | 129.9 | 625.1 | 2652.8 | WNT1 inducible signaling pathway protein 1 |
| 208079_s_at | STK6 | 6790 | | 202.1 | 1001.8 | 933.1 | 359.6 | 846 | serine/threonine kinase 6 |
| 203180_s_at | ALDH1A2 | 8854 | | 37.7 | 725.3 | 108.2 | 950.7 | 140.6 | aldehyde dehydrogenase 1 family, member A2 |
| 226425_at | EPHB1 | 2047 | | 335.1 | 102.6 | 139.3 | 384.1 | | EPH receptor B1 |

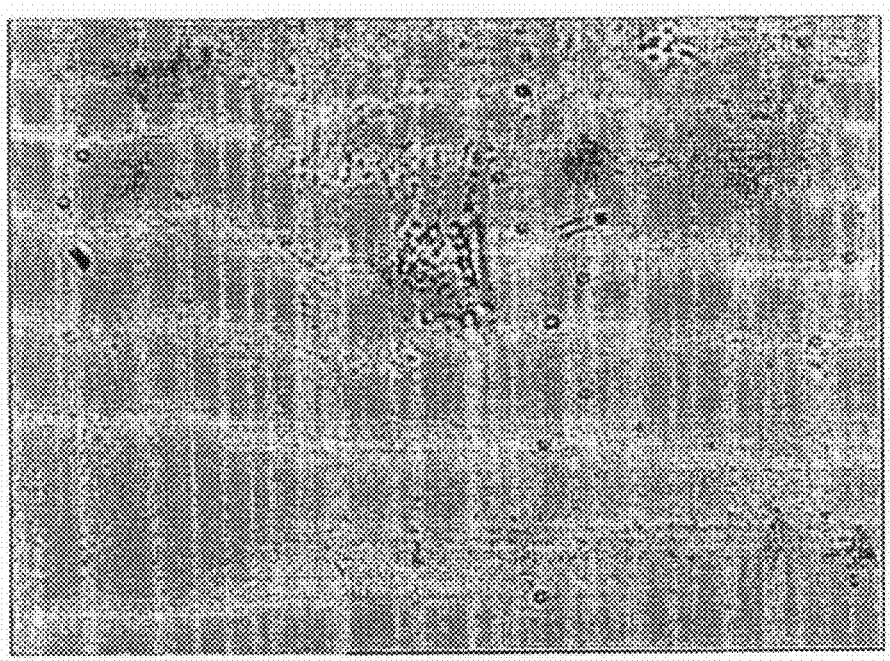
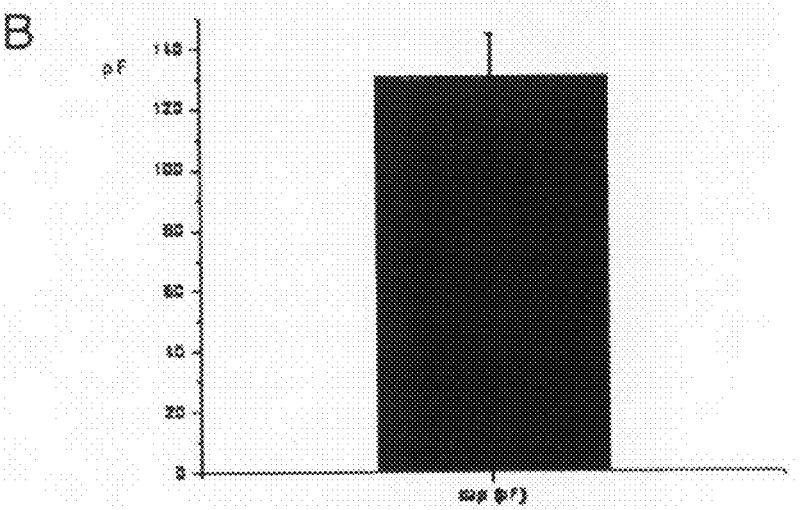
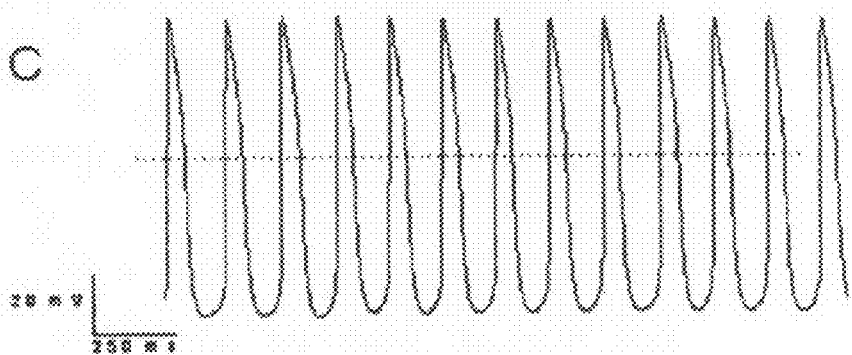
Fig. 14

SKELETAL MUSCLE PERIANGIOBLASTS AND CARDIAC MESANGIOBLASTS, METHOD FOR ISOLATION AND USES THEREOF

BACKGROUND OF THE INVENTION

Stem Cells of Skeletal Muscle

The quest for a cell able to restore muscle structure and function in dystrophic patients started in 1961 with the identification of satellite cells (1). Although satellite cells remain the cell type that by and large retain the main myogenic activity in adult muscle (2, 3), some of their biological features limit their potential use for the treatment of primary myopathies. In fact satellite cells lack the ability to cross the muscle endothelium when delivered systemically and must be injected intramuscularly every 2 $mm^3$ of all, or at least of life essential, muscles of the patients, since this is the maximal distance they apparently can migrate from the site of injection (4). This feature alone makes their use in cell therapy protocols extremely difficult, at least with current technology, also considering that the large majority of injected cells are lost within the first day (5). A second problem is represented by the reduced proliferation potency of satellite cells from dystrophic patients and also by the recent observation that in vitro expansion reduces their in vivo differentiation potency (6).

The demonstration that other cell types, resident in the bone marrow or in the vascular niche of other tissues, can differentiate into skeletal muscle in vitro or in vivo created an alternative possibility for the cell therapy of muscular dystrophy (7). The ideal cell population should be i) easily obtainable from accessible anatomical sites, ii) expandable in vitro to the large number of cells required for systemic treatment ($10^9$ or more), iii) easily transducible with viral vectors, vi) able to reach skeletal muscle through a systemic route and, finally v) able to differentiate into skeletal muscle cells in vivo while maintaining a self-renewal ability. Of the many types of recently identified and characterized mesoderm stem cells, many show one or more of these features. However, in general their characteristics have not been investigated systematically. By contrast, embryonic mouse mesoangioblasts have been shown to restore muscle morphology and function in a mouse model of muscular dystrophy (8). Human and mouse cells dramatically differ in the ability to extensively proliferate in vitro and it is therefore essential to test whether human cells corresponding to embryonic mouse mesoangioblasts exist in fetal or post-natal human tissues and, if so, whether they show features that may allow to predict a successful use in cell therapy protocols for muscular dystrophy.

In the present study, the cells originating from normal and dystrophic adult human skeletal muscle are named periangioblasts, and can be expanded in vitro for about 20 population doublings before undergoing senescence as diploid non tumorigenic cells; they can be transduced with viral vectors expressing mini dystrophin or other therapeutic genes and then induced to differentiate into skeletal muscle.

When transplanted into dystrophic immune-incompetent mice they give rise to large numbers of new fibers expressing human dystrophin. The cells of the present invention, differ from any other mesoderm stem/progenitor cells because of a) their source (blood vessels), b) their method of isolation (explant rather than proteolytic digestion) and c) their myogenic differentiation potency which is strikingly higher than any other cell in the body, beside resident satellite cells.

Periangioblasts express some of the proteins that leukocytes use to adhere to and cross the endothelium and thus can diffuse into the interstitium of skeletal muscle when delivered intra-arterially. This is a distinct advantage over resident satellite cells that cannot do the same.

Therefore catheter mediated delivery to the succlavia, the diaphragmatic and the iliac arteries should allow periangioblasts from skeletal muscle to reach and colonize muscles that are essential for motility and breathing.

More importantly, when induce to differentiate in vitro, periangioblasts spontaneously differentiate up to 40% of the population, an efficiency far superior to any other non myogenic cell tested so far and second only to resident satellite cells which however cannot be delivered through the circulation. Although not yet tested in a systematic comparative way, the number of dystrophin positive muscle fibers produced in vivo by periangioblasts is far higher than what reported previously by other authors.

Thus, the human cell periangioblast population of the present invention fulfils all the criteria for a successfully cell therapy protocol in muscular disorders such as Duchenne muscular dystrophy. Periangioblasts can be easily isolated from the biopsy that is used for diagnosis. A needle biopsy is a tolerable surgery that can be repeated every few years to further the protocol therapy.

Stem Cells of Cardiac Muscle

The post-infarction ventricular remodeling is characterized by progressive expansion of the initial infarct area and of the left ventricular lumen, with cardiomyocyte replacement by fibrous tissue deposition in the ventricular wall. One approach proposed to reverse myocardial remodeling is regeneration of cardiac myocytes using stem cells (35). Different groups have already reported the isolation of cardiac stem-like cells based on distinct cell surface markers such as Sca-1 or c-Kit (36, 37); these cells are able to restore cardiac function after ischemic injury although with variable efficacy. However their spontaneous cardiac differentiation is low and they also differentiate into other tissue types of the heart (36-39) suggesting that they represent the in vitro expansion of a pluripotent progenitor, that still requires specific signals to undergo terminal cardiac differentiation. On the other hand, Isl-1 expressing progenitors appear to be committed to cardiac differentiation only but still require interactions with other. cells for both proliferation and differentiation (38). The emerging scenario reveals an unforeseen complexity where different types of progenitors may be identified and eventually isolated at different stages of their differentiation process. It is also becoming clear that a significant part of the beneficial effect that most of these cells exert on the infarcted heart is due to the secretion of factors that increase survival of residual myocardium and/or favor angiogenesis (40). This was for example the case of embryonic mesoangioblasts whose transplantation resulted in a 50% recovery of cardiac function but whose differentiation into new cardiomyocytes was rare (41).

In the present invention, adult mouse and human cardiac muscle biopsies were performed allowing, through mechanical and not enzymatic dissociation method, the isolation of cells denominated adult cardiac mesoangioblasts. It was assumed based on previous studies on cells from skeletal muscle, that a local commitment of adult cells may result in more efficient cardiac differentiation than that previously observed with embryonic mesoangioblasts. Indeed, mouse cardiac mesoangioblasts show spontaneous (without chemical adjuvants) and high differentiation rate into beating cardiomyocytes while displaying only a low differentiation rate into smooth muscle cells. As for human cardiac mesoangioblasts, they show high differentiation into beating cardiomyocytes rate in the presence of 5-azatydine or when co-cultured with rat neonatal cardiomyocytes and only low differentiation rate into smooth muscle cells.

In the case of mouse cardiac mesoangioblasts, the efficiency of spontaneous cardiac differentiation is amazingly high and superior to already described cardiac stem cells (Anversa group, patent application WO 02/09650), Isl-1 positive cardioblasts (Chien group), Tert/Sca1+ progenitors (Schneider group, patent application WO 04/019767) and not even comparable to other types of stem cells whose cardiac differentiation ability is only anecdotic. Concerning their phenotype, mouse cardiac mesoangioblasts differ from all the other cardiac stem cells: a) they express CD34 and CD31 which is different from cardiac stem cells and Isl-2 cardioblasts; b) they express c-Kit and Nkx 2.5 which is different from Tert/Sca1 progenitors.

Human cardiac mesoangioblasts expressed similar markers and genes as mouse cardiac mesoangioblasts but these cells are only able to differentiate into cardiomyocytes in presence of 5-azatydine or in co-culture with rat neonatal cardiomyocytes.

Patents U.S. Pat. Nos. 5,486,359 and 6,184,035 describe human mesenchymal stem cells and methods for isolation and activation thereof, and control of differentiation from skeletal muscle stem or progenitor cells. The cells described in these patents are very different from the one of the present invention, in particular regarding the presence or absence of specific markers.

DESCRIPTION OF THE INVENTION

The present invention describes the isolation and characterization of human cells similar to, but distinct from previously described mesoangioblasts (9) from both skeletal and cardiac muscle. In addition, the authors demonstrated that cells isolated either from adult skeletal muscle (herein named periangioblasts) and adult cardiac muscle (herein named cardiac mesoangioblasts) fulfill all the criteria requested for attempts to treat muscular disorders including muscular dystrophy and cardiopathies, respectively.

Indeed, the invention describes the isolation of periangioblasts and cardiac mesoangioblasts from biopsies of mammalian adult skeletal or cardiac muscles, respectively.

Therefore it is an object of the present invention a skeletal muscle periangioblast cell population characterized by expressing the following marker phenotype: $CD31^-$, $CD34^-$, $CD45^-$, $CD62L^-$, $CD106^-$, $CD117^-$, $CD133^-$ $CD146^+$, $CD49b^+$, $CD13^+$ and $CD44^+$. Preferably, the skeletal muscle periangioblast cell population further expresses at least a protein belonging to the following group: VCAM-1 (vascular cell adhesion molecule), ICAM-1/5/2(inducible cell adhesion molecule), CD36, CD44, b7, b5, b1, b2 integrins, a integrins (some a1, a5 and a6), LFA-1 (leukocyte factor antigen), IL-1R (interleukin-1, receptor), SDF-R (stromal derived factor, receptor) or Cadherins. More preferably, the skeletal muscle periangioblast cell population is able to spontaneously differentiate in vitro in the myogenic lineage in suitable culture conditions, as culturing in a less rich medium, with no inducing agents. Even more preferably, the skeletal muscle periangioblast cell population is genetically modified so as to express an exogenous coding sequence. Preferably the exogenous coding sequence encodes for a dystrophin protein or a derivative thereof. More preferably the exogenous coding sequence encodes for a mini-dystrophin protein.

It is a further object of the invention the use of the periangioblast cell population defined above for the cell therapy treatment of muscular disorders, as muscular dystrophy. Preferably, the muscular dystrophy is selected from the group of: Duchenne muscular dystrophy, Becker muscular dystrophy, facioscapulohumeral muscular dystrophy, myotonic muscular dystrophy, limb-girdle muscular dystrophy, oculopharyngeal muscular dystrophy, Emery-Dreifuss muscular dystrophy, distal muscular dystrophy or congenital muscular dystrophy. Alternatively the muscular disorder may be a muscular myopathy.

It is a further object of the invention the use of the periangioblast cell population defined above for muscular disorder therapeutic drug screening.

Another object of the invention is an in vitro method for isolating a skeletal muscle periangioblast cell population defined above from a tissue sample of a donor, comprising the steps of:
a) allowing dissociation of cells from the tissue sample by non proteolytic digestion means;
b) culturing dissociated cells in a mammalian cell growth medium including growth factors, amino acids, trace elements, non essential amino acids, fetal calf serum and b-FGF.

Preferably, the growth medium is the MegaCell® DMEM or the Iscov® medium. More preferably, the in vitro method further comprises the step of incubating cultured extracted cells with Sdf-1 or TNFα.

Preferably, the donor is an healthy or a disease-affected subject. More preferably, the subject is affected by muscular dystrophy. Even more preferably, the muscular dystrophy is Duchenne muscular dystrophy.

It is a further object of the invention a human cardiac muscle mesoangioblast cell population characterized by expressing the following marker phenotype: $CD31^+$, $CD34^+$, $CD44^+$, $CD117^+$, $CD45^-$ and $CD133^-$. Preferably the human cardiac muscle mesoangioblast cell population further expresses the following marker phenotype: $Nkx2.5^+$, $Gata4^+$, $Mef2A^+$, $Tbx2^+$, $Tbx5^+$ and $Isl-1^-$. More preferably the human cardiac muscle mesoangioblast cell population is able to spontaneously differentiate in vitro in cardiomyocytes in suitable culture conditions. Differentiation into cardiac cells may be induced either by exposing cells to 5-azacytidine or by co-culturing human cardiac mesoangioblasts with neonatal cardiomyocytes. In order to distinguish between the populations, mouse or rat neonatal cardiomyocytes may be utilized.

It is another object of the invention the use of the human cardiac muscle mesoangioblast cell population as defined above for the cell therapy treatment of cardiac diseases. Preferably, the cardiac disease results from cardiac necrosis or hypertrophy. Preferably the cardiac disease is a dilatative cardiopathology or a valvular pathology.

It is a further object of the invention a mouse cardiac muscle mesoangioblast cell population characterized by expressing the following marker phenotype: $CD31^+$, $CD34^+$, $CD44^+$, $Sca-1^+$, $c-kit^+$ and $CD45^-$. Preferably, the mouse cardiac muscle mesoangioblast cell population further expresses the following marker phenotype: $Nkx2.5^+$, $Gata4^+$, $Gata6^+$, $Tbx2^+$, $Tbx5^+$, $Isl-1^+$ and $Mef2A^-$. More preferably, the mouse cardiac muscle mesoangioblast cell population is able to differentiate in vitro in cardiomyocytes in suitable culture conditions. Differentiation into cardiac cells may be induced either by exposing cells to 5-azacytidine or by co-culturing mouse cardiac mesoangioblasts with neonatal cardiomyocytes. In order to distinguish between the populations, mouse or rat neonatal cardiomyocytes may be utilized.

Another object of the invention is the use of the mouse cardiac muscle mesoangioblast cell population as defined above for cardiac diseases therapeutic drug screening.

It is a further object of the invention an in vitro method for isolating a mouse or human cardiac muscle mesoangioblast cell population as defined above from a tissue sample of a donor according, comprising the steps of:
a) allowing dissociation of cells from the tissue sample by non proteolytic digestion means;
b) culturing dissociated cells in a mammalian cell growth medium in the presence of a non adhering coating.

Preferably, the donor is a healthy or a disease-affected subject. More preferably, the subject is affected by atrial valvular dysfunction.

The invention will be now described by non limiting examples referring to the following figures:

FIG. 1. In vitro characterization of human periangioblats. A: Phase contrast morphology of the cellular outgrowth of a fragment of interstitial tissue containing a small vessel cultured from a biopsy of normal adult human muscle. Note the presence of round and refractile cells on top of a layer of fibroblast-like cells. B: phase contrast morphology of a polyclonal population isolated from a normal adult human skeletal muscle explant culture after 5 passages in vitro. C: Cariotype of human normal periangioblasts after 15 passages, showing an euploid number of chromosomes. D: Proliferation curves of two different normal (open symbols') and two dystrophic (closed symbols) human periangioblasts. E: telomerase activity of human normal periangioblasts (right side of the panel) at passage VIII°, XII° and XIX°. Human carcinoma cells, HI299, are also shown as a positive control in the left side. The arrow indicates the first ladder of polymerase addition product; the black arrowhead shows non specific amplification products, present in all samples while the gray arrowhead shows the internal TRAP assay standard. F: Average telomere length from cells at passage VIII°, XI° and XIX° (lanes 1, 2, 3 respectively) showing progressive shortening.

FIG. 2: A: In vitro characterization of normal human periangioblasts. Phase contrast morphology of the same polyclonal population exposed to different combinations of growth factors: A: none; B: FGF; C: FGF+PDGFbb; D: FGF+ EGF; E: FGF+LIF; F: FGF+IGF1.

Figure 3:
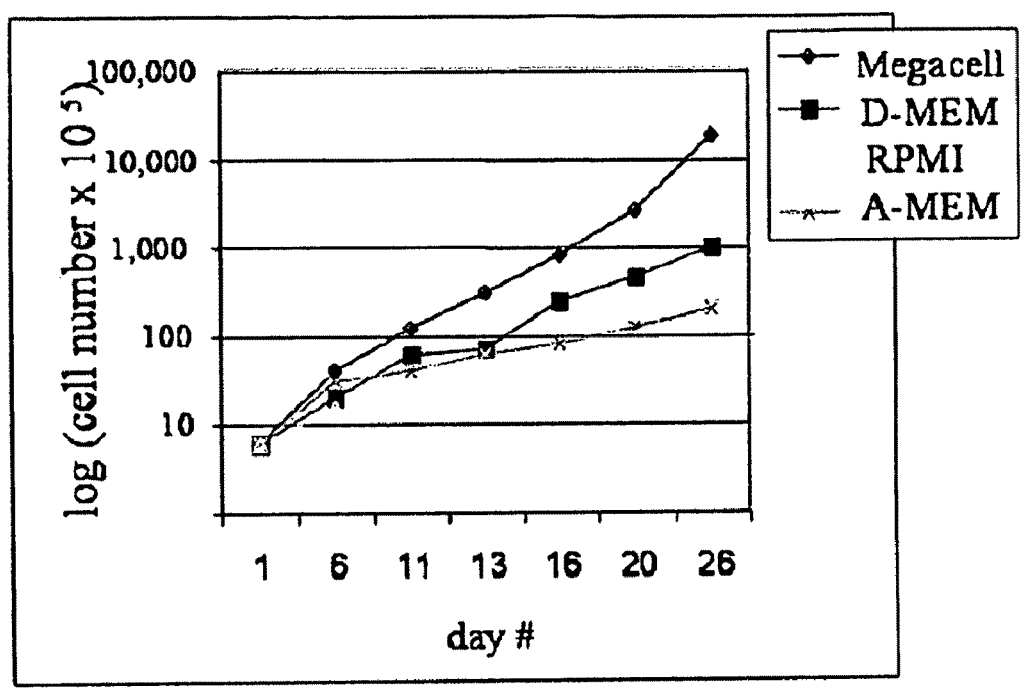

FIG. 3: Growth curve of normal human periangioblasts growing in presence of different mediums: Megacell, D-MEM, RPMI or A-MEM.

Figure 4:
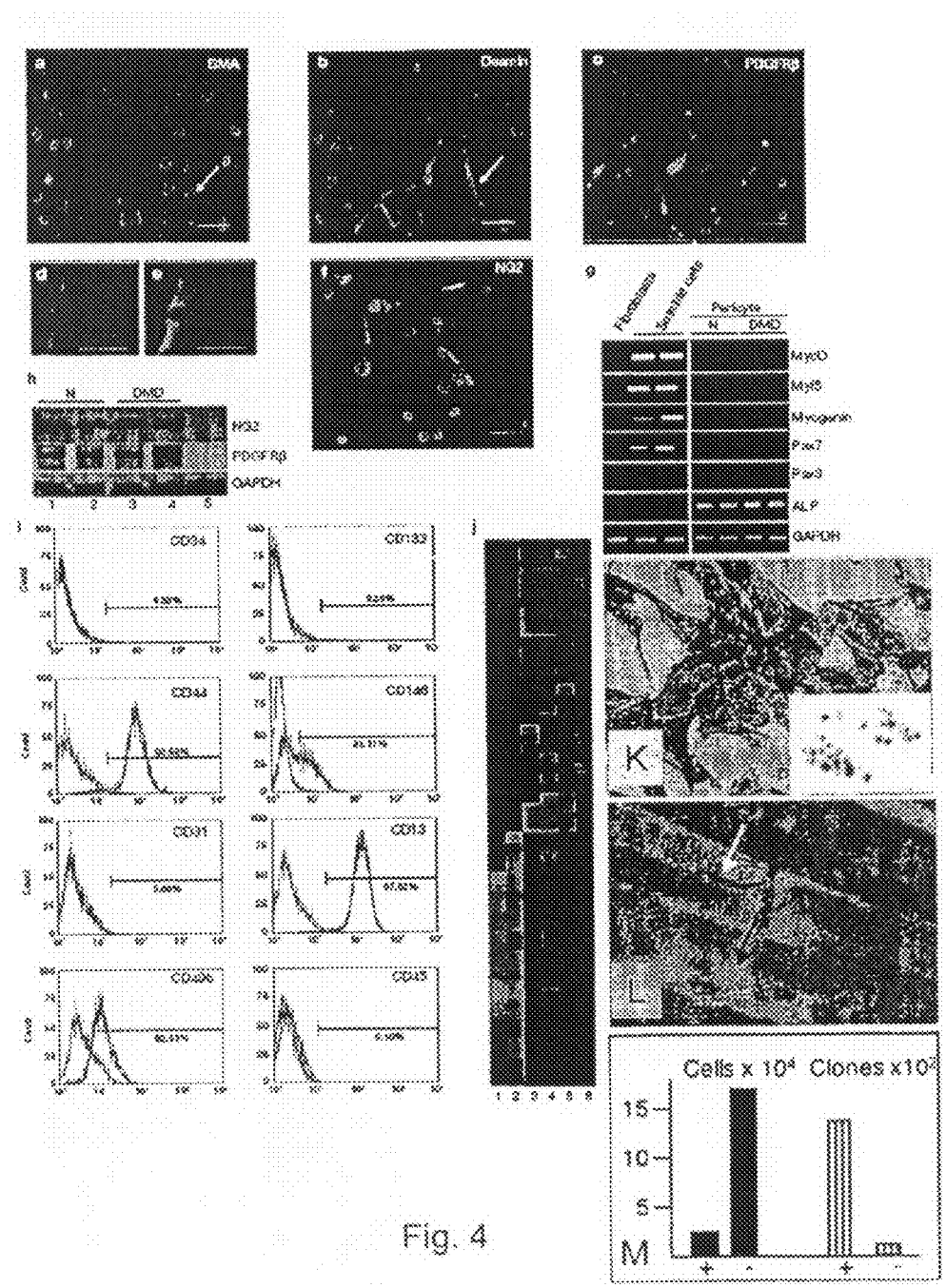

FIG. 4: Phenotype of human adult periangioblasts. (a-f) Immunofluorescence analysis with anti-SMA (a) and anti-desmin (b) antibodies, revealing expression in approximately 10% of the population and in some cases the cells co-express these two markers (arrows); an anti-PDGF receptor beta (c) stains the majority of the cells at the cell surface, as detailed in (d) and (e) (which also shows co-staining with anti-SMA) and anti-NG2 (f); nuclei are stained with DAPI. (g) RT-PCR analysis of the expression MyoD, Myf5, Myogenin, Pax7, Pax3, and ALP in human fibroblasts, satellite cells, normal (N) and DMD periangioblasts Control GAPDH is also shown. (h) Western blot analysis of NG2 proteoglycan and PDGF R beta in extracts from periangioblasts. Isolated from normal (lanes 1,2) and DMD (lanes 3,4) muscle. Human normal muscle extract is also shown (lane 5) as a negative control. GAPDH is shown for sample normalization. (i) FACS analysis of human periangioblasts using a panel of CD antibodies (CD34, CD133, CD44, CD146, CD31, CD13, CD49b, CD45). (j) Micro-array analysis showing significant genes differentially expressed between DMD (lanes 1,2), normal (lanes 3,4) polyclonal population of periangioblasts. Lanes 5 and 6 show the profile of differentially expressed genes in two individual clones from the polyclonal population shown in lane 3. (a, b, c, d, e and f) Bar=20 μm. (K): Staining for alkaline phosphatase (AP) revealing expression at varying levels in 100% of the cell population. The inset shows floating cells, just removed from the explant (as shown in FIG. 1A) all of which also express AP. L: Expression of AP in muscle section, showing activity in small arteries (white arrows) but not in venules (black arrow). M: Distribution of AP+ (blue solid bars) and AP− (red solid bars) cells isolated from adult normal human skeletal muscle. Cloning efficiency of the of AP+ (blue dashed bars) and AP− (red dashed bars) previously sorted cells.

Figure 5:
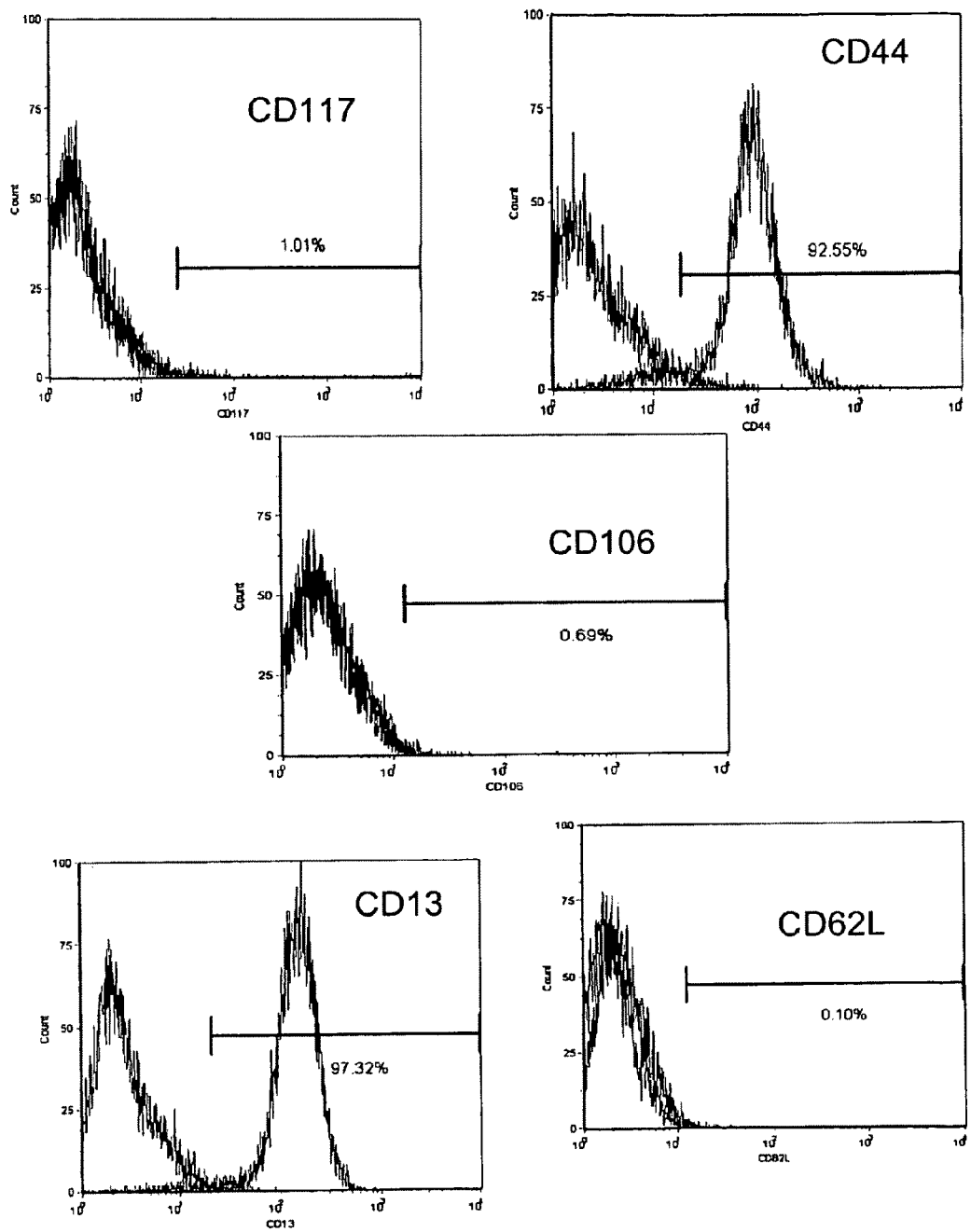

FIG. 5: Surface markers expression analyzed by flow cytometry. Normal human periangioblasts were analyzed for the presence of CD117, CD44, CD106, CD13 or CD62L.

FIG. 6: Expression profiles of genes differentially expressed in two populations of Duchenne (DMD3 and DMDA) and normal (MIX40Y and MIX78Y) human periangioblasts, and in two clonal isolates from MIX78Y (CL9 and CLB). Only genes whose expression varies at least by 3 fold among all the Duchenne and normal cells are shown.

Figure 7:
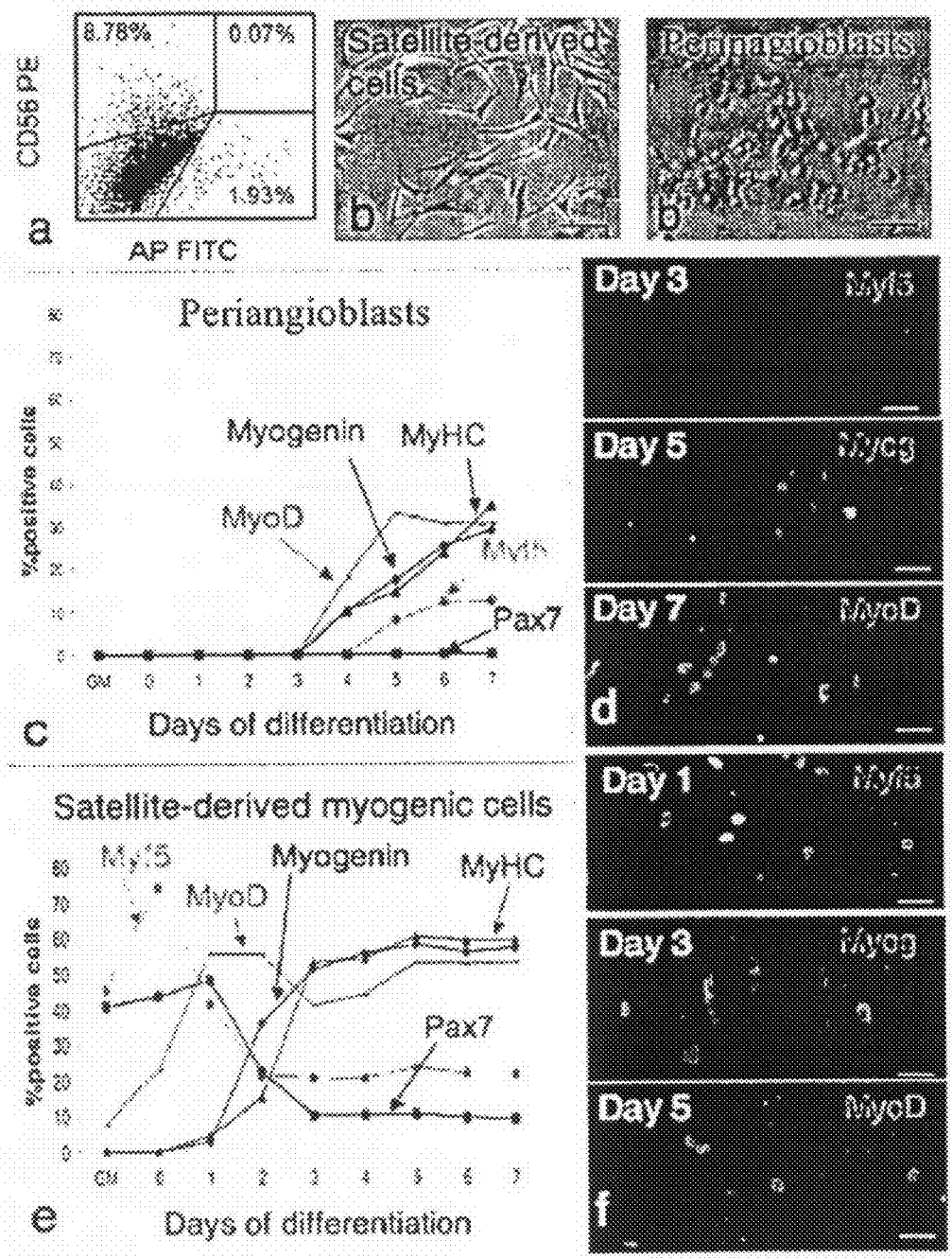

FIG. 7: Time course of myogenic differentiation in cultures of human periangioblasts and satellite cell derived myogenic precursors. Cells were digested from human skeletal muscle and FACS sorted (a) into a CD56+, satellite cells and ALP+, periangioblasts which were separately cultured under myogenic promoting conditions. Phase contrast morphology of the two cell types at day 1 in culture is shown in b and b' respectively. Cultures were fixed and stained daily with antibodies against Pax7, Myf5, MyoD, Myogenin and Myosin heavy chains (MyHC): examples are shown in d for periangioblasts and in f for satellite cells. Bar=20 μm. Positive cells were counted in 20 randomly selected fields and calculated as percentage of total nuclei visualized by DAPI. The time course of expression of these different proteins are shown for periangioblasts (c) and for satellite cells (e).

Figure 8:
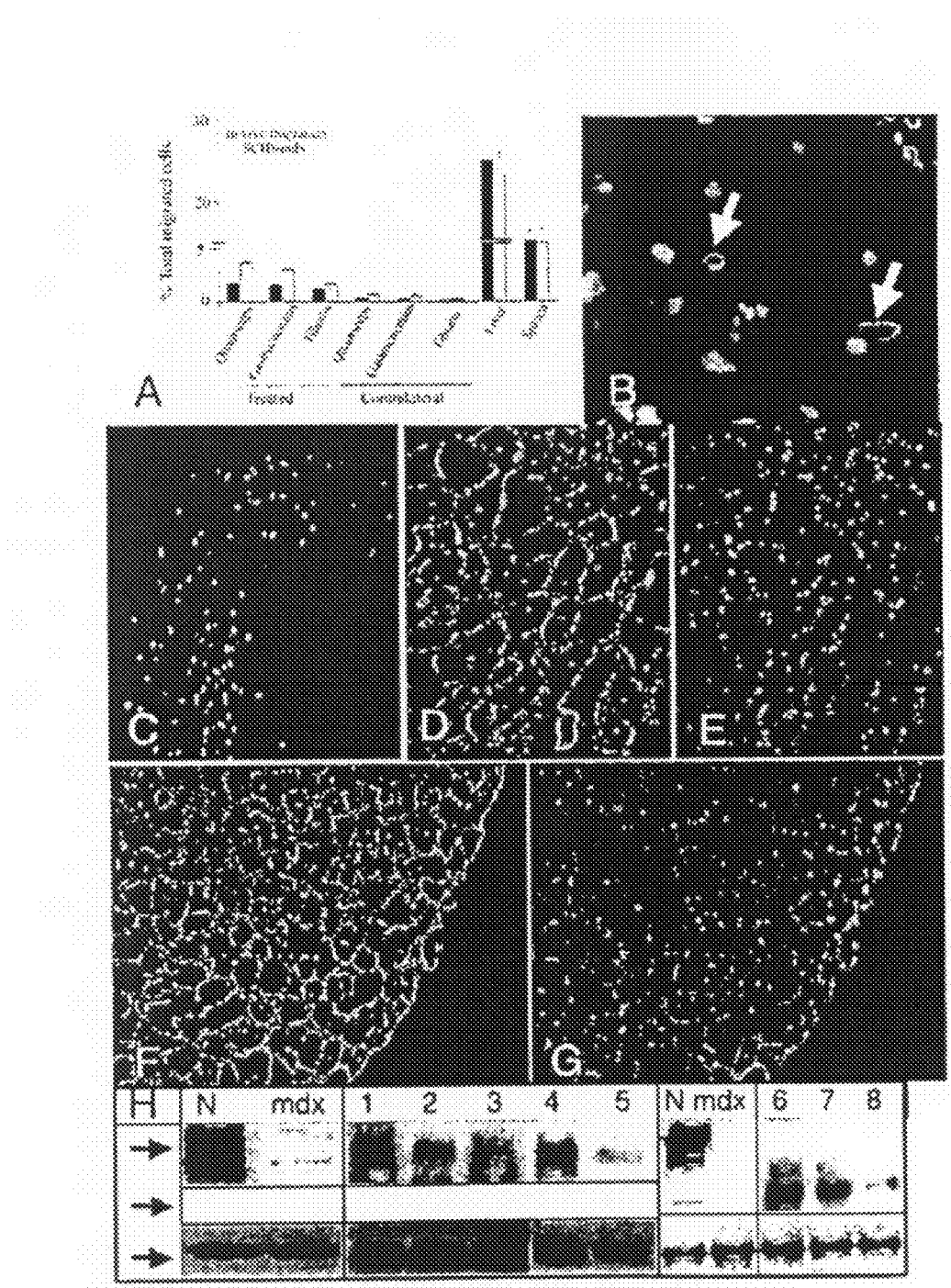

FIG. 8: Tissue distribution and differentiation of human periangioblasts in dystrophic muscle. A: In vivo periangioblasts homing. $5 \times 10^5$ mouse (black bars) or human (gray bars) male periangioblasts injected into the right femoral artery (treated muscles) of 2-months-old female mdx/SCID mice. After 6 h different organs were collected and the percentage of migrated cells was calculated by real time PCR for Y chromosome. A mean of three independent experiments run in triplicate is shown. B: High magnification of two human nuclei (lamin A/C positive: green), localized underneath the basal lamina of muscle fibers, stained with anti-laminin (red) antibodies. Nuclei are stained with DAPI. C: low magnification of a similar field, showing many human nuclei (lamin A/C positive: green) in the interstitium and inside muscle fibers, stained with anti-laminin (red) antibodies. D, E: Immunofluorescence analysis of mdx/SCID mice, 1 month after transplantation of $5 \times 10^5$ human normal periangioblasts and stained with antibodies against laminin (green) and human dystrophin (Dys3: red). F,G: Immunofluorescence analysis of mdx/SCID mice, 1 month after transplantation of $5 \times 10^5$ human DMD periangioblasts (in vitro transduced with a lentiviral vector expressing human mini-dystrophin) and stained with antibodies against laminin (green) and human dystrophin. H: The western blot analysis of human dystrophin expressed in muscles from different mice transplanted with $5 \times 10^5$ human normal (lanes 1-5) and dystrophic, corrected (lanes 6-8) periangioblasts. Normal (N) and DMD skeletal muscle (mdx) are shown as controls. Black arrow indicates wt dystrophin, red arrow indicates mini-dystrophin and blue arrow indicates myosin heavy chains, shown as loading control.

Figure 9:
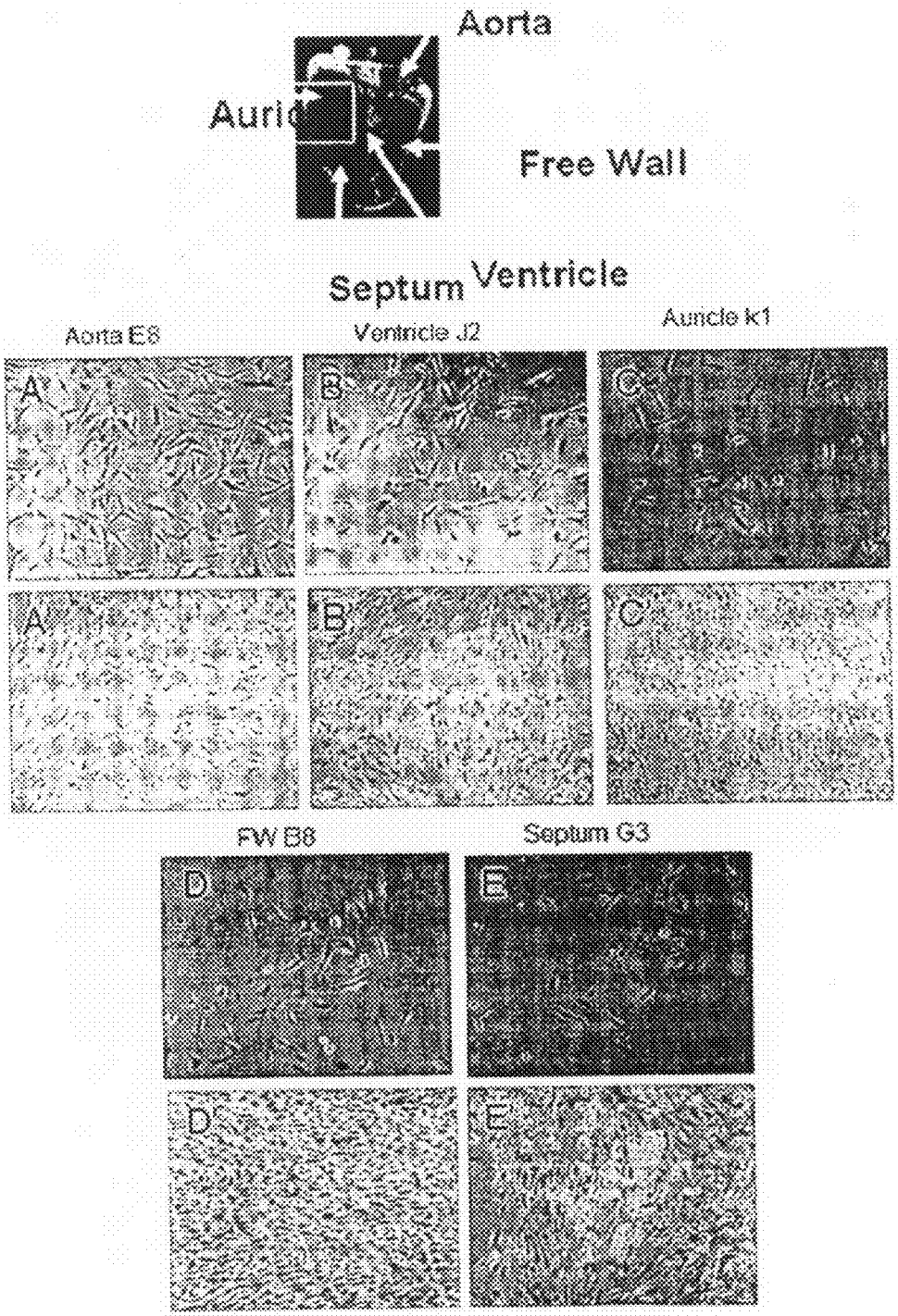

FIG. 9: Adult mouse cardiac mesoangioblasts isolated from explants of different heart regions. Phase contrast morphology of growing (A-E) or confluent (A'-E') cardiac clones isolated from aorta (A, A'), ventricle (B, B'), auricle (C, C'), free wall (D, D') or septum (E, E').

Figure 10:
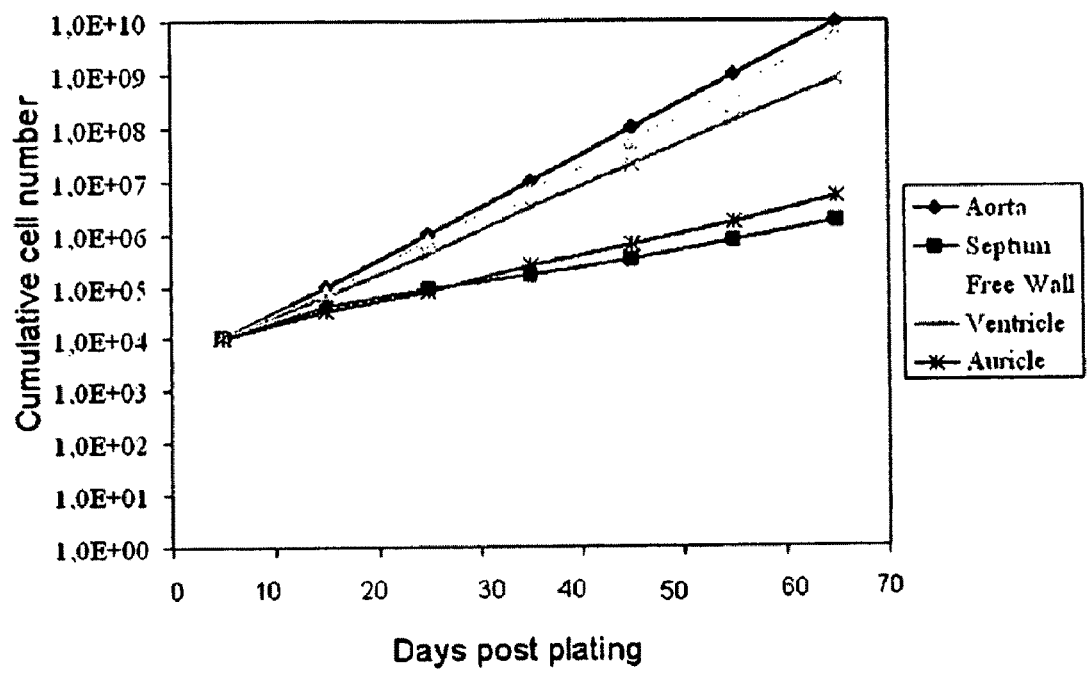

FIG. 10: Growth curve of the five different origins mouse cardiac clones in complete DMEM (with 20% FCS). Note that clones obtained from aorta, free wall or ventricle have a higher proliferative rate than those from auricle or septum.

Figure 11:
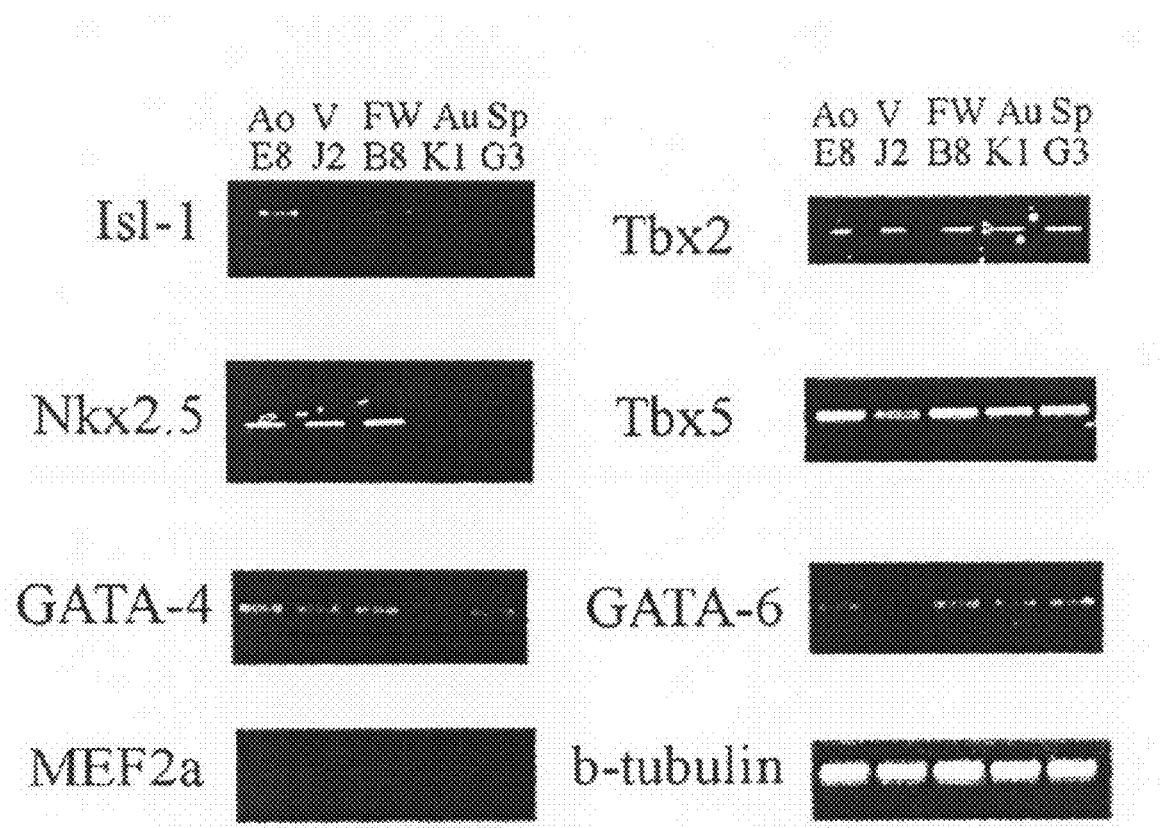

FIG. 11: Expression of cardiac progenitor markers analyzed by PCR. RNA extracted from the different mouse cardiac clones cells was analyzed for the presence of cardiac markers genes: isl-1, nkx 2.5, GATA-4/6, MEF2a and Tbx2/5 by PCR. Note the different expresion pattern between clones in nkx2.5.

Figure 12:
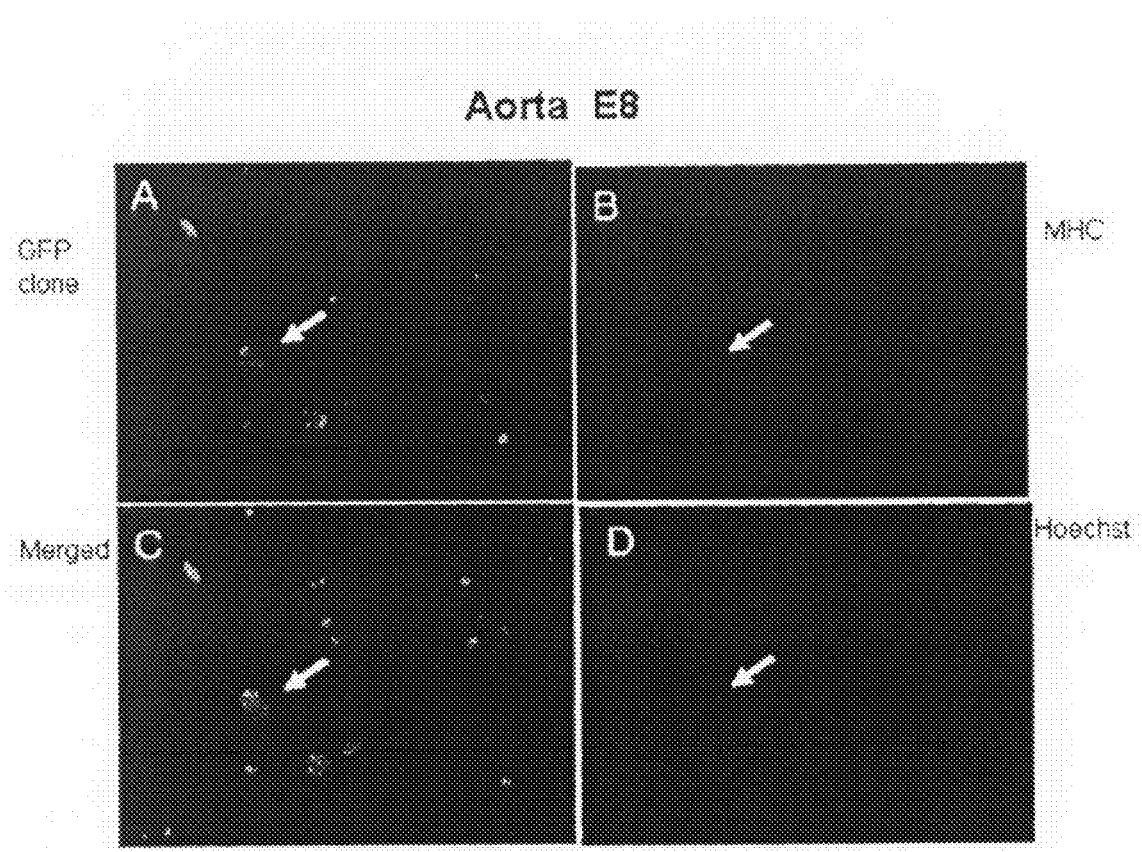

FIG. 12: Differentiation of mouse cardiac mesoangioblast clones co-cultured with rat cardiomyocytes. GFP expressing aorta cardiac clone cells were co-cultured with rat cardiomyocytes for five days and then analyzed for the expression of myosin, MyHC (red). Nuclei were stained with Hoechst.

Figure 13:
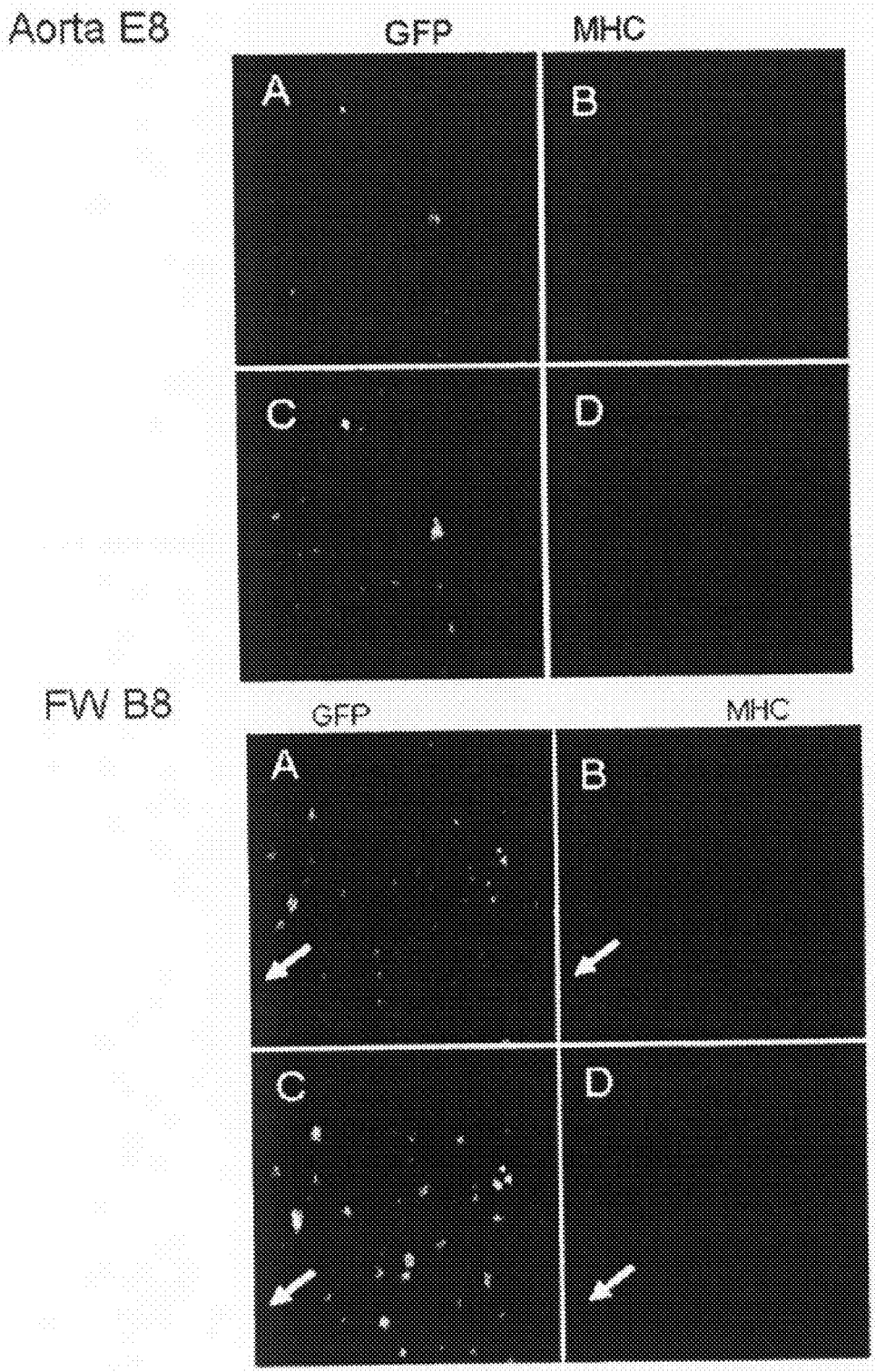

FIG. 13: Spontaneous differentiation of mouse cardiac mesoangioblast clones. GFP expressing aorta or free wall mouse cardiac clones cells differentiated with low serum DMEM for five days and analyzed for the presence of myosin, MHC (red). Nuclei were stained with Hoechst.

FIG. 14: Electrophysiology studies of mouse ventricle cardiac mesoangioblast clone cells. A. Image of a mouse beating ventricle cardiac clone while making patch-clamp measurements. B. Cell capacitance of a ventricle cardiac clone (134.5+−6.8 pF). C. In the current-clamp mode, action potentials the authors recorded at physiological temperatures at 1 Hz. A representative action potencial waveforms of a ventricle cardiac clone.

Figure 15:
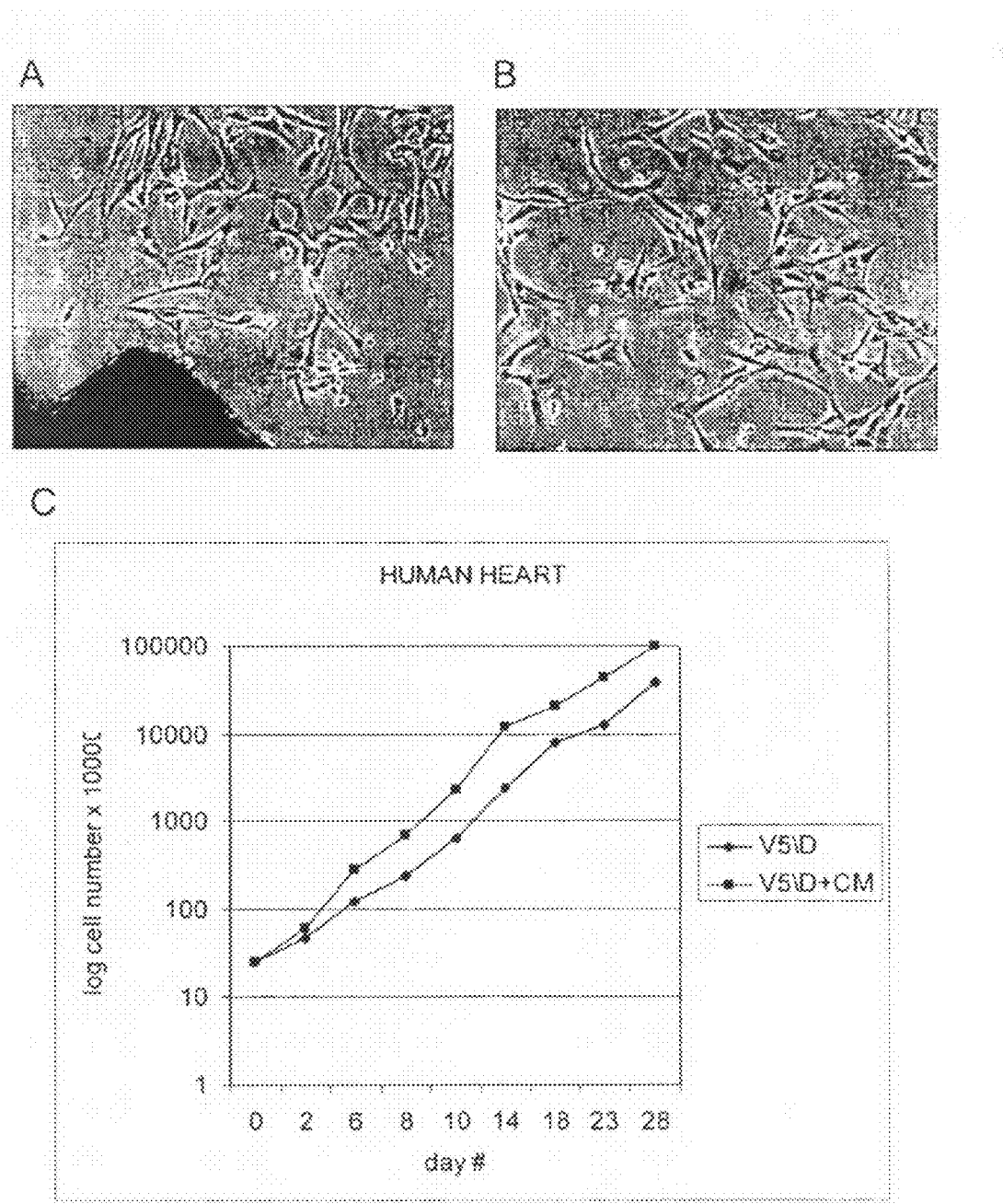

FIG. 15: Human cardiac mesoangioblasts growing after dissecting explants. (A, B) Phase contrast morphology of growing cells isolated from human heart. (C) Growth curve of human cardiac mesoangioblasts in different medium V5D: Cells from Ventricular biopsy (patient n° 5) grown in DMEM; V5D+CM: same cells grown in DMEM supplemented with Conditioned Medium from the same confluent cells.

Figure 16:
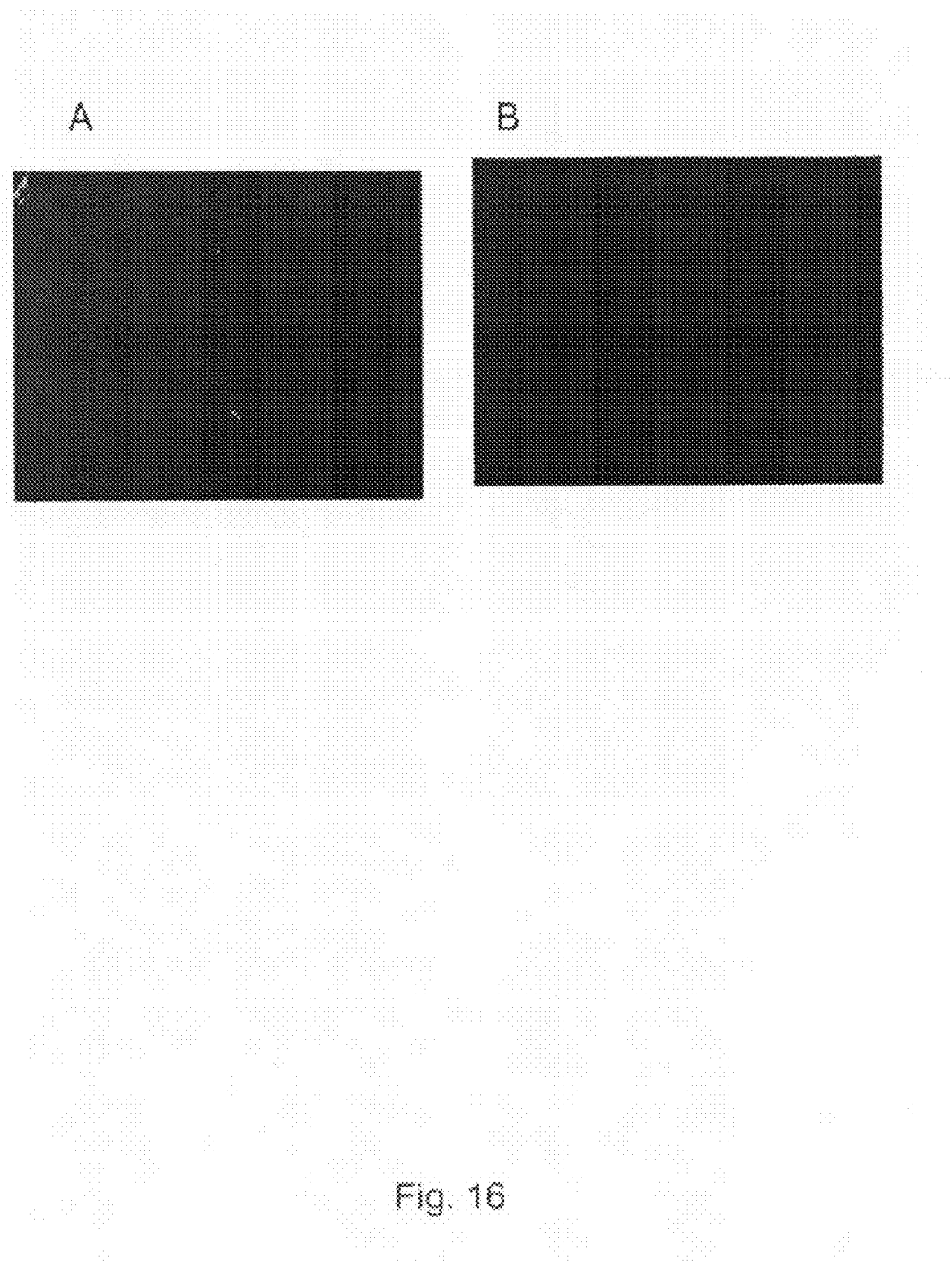

FIG. 16: Human cardiac mesoangioblasts from two different patients differentiated to cardiomyocytes and expressing cardiac actin.

SKELETAL MUSCLE PERIANGIOBLASTS

Methods
Isolation and Culture of Periangioblasts

Cells were prepared from ten patients undergoing diagnostic biopsy and later classified as non-dystrophic (and non affected by secondary myopathies) and from six DMD patients, ranging in age from 15 to 78 years (non DMD) and 3 to 8 years (DMD). The muscle samples (100-200 mg) from needle biopsies of the biceps brachialis were stored in DMEM without FCS, with antibiotics and kept at 4° C. for maximum 24 h prior to dissection. The muscle sample was rinsed in PBS with $Ca^{2+}/Mg^{2+}$ (from Sigma) and sharply dissected into 1-2 mm diameter pieces with a scalpel. Fragments of interstitial tissues containing small vessels were transferred to a Petri dish coated with type I collagen (1 mg/ml in 0.1 M acetic acid). No care was taken to clean the vessels from surrounding mesenchyme and fragments of muscle fibers. The medium consisted of MegaCell® DMEM (Sigma, M3942) supplemented with 5% FCS, 5 ng/ml bFGF (Peprotec 100-18B), 2 mM glutamine, 0.1 mM beta mercaptoethanol, 1% non essential amino acids, 100 IU/ml penicillin and 100 mg/ml streptomycin. The tissue fragments were cultured for 7-8 days. After the initial outgrowth of fibroblast like cells, small round and refractile cells appeared. Because of their poor adhesion (many of these cells were floating) this cell population was easily collected by gently pipetting of the original culture and plated on collagen coated dishes at a density of $5 \times 10^4$ cell/30 mm dish. The cells were either grown as a polyclonal population or cloned by limiting dilution on type I collagen (Sigma C9791) coated dishes.

Alternatively MegaCell® DMEM can be replaced by the Iscov® Media (GIBCO, 12440-053). alpha-MEM, DMEM, RPMI, F12 were unable to support proliferation of periangioblasts.

Karyotype Analysis

Human perioangioblasts, plated at ⅓ confluence 72 hr before analysis, were processed with the Karyomax kit (Invitrogen) according to the manufacturer's instructions. For each of the karyotypes analyzed, 5 different metaphase spreads were examined.

Telomerase Activity and Telomere Length Analysis

Telomerase activity was determined using the TRAP assay as described previously (29). Telomere length was measured after DNA extraction from human perioangioblasts cell samples with different population doublings by digestion with the restriction enzymes AluI, CfoI, HaeIII, HinfI, MspI, and RsaI and electrophoresis on 0.7% agarose gels as detailed elsewhere (30). The gels were denatured, dried, and neutralized, and the signal was detected in situ by using a telomeric probe end-labeled with [−32P]ATP. After hybridizing to radiolabeled probes, signals were analyzed with the program Telorun, using mean calculations designed to normalize signal intensity relative to the digestion product size.

Tumorigenicity

To test for possible tumor formation, 10 nude (from Charles River) and 10 SCID mice (from Charles River) were injected subcutaneously with $10^7$ normal human periangioblasts. The same number of mice were similarly injected with $10^7$ DMD human periangioblasts, previously transduced with a lentiviral vector expressing human mini-dystrophin. After 12 months mice were sacrificed and analyzed for the presence of macroscopically detectable tumors. No tumor was detected in any injected animal.

Cell Transduction with Lentiviral Vectors

Cells were transduced as described before (8) with third generation lentiviral vectors expressing nuclear LacZ or GFP or human mini-dystrophin (31).

Differentiation Assays

Differentiation into smooth muscle cells and osteoblasts was induced by treatment with $TGF\beta_1$ and BMP2 respectively, as previously described (9). Differentiation into skeletal muscle cells was induced by co-culturing human periangioblasts with C2C12 mouse myoblasts. Human periangioblasts were added at 1:5 ratio and cultures were shifted to differentiation medium (DMEM supplemented with 2% horse serum). After 5 days, cultures were fixed and stained with antibodies against striated myosin (MF20) and human lamin A/C. Identification of human nuclei was confirmed by DAPI. Percentage of myogenic differentiation was calculated by counting the number of human nuclei within myosin positive cells as percentage of total human nuclei. Biochemical differentiation was confirmed by RT-PCR using human specific oligonucleotides for MyoD and Nkx2.5 respectively.

Spontaneous skeletal myogenic differentiation of human periangioblasts was induced by plating cells onto matrigel coated dishes in differentiation medium. After 7 days, cultures were fixed and stained with antibodies against striated myosin (MF20) and Myf5. Western blot analysis was performed using the same antibodies. Human satellite cells, used as a positive control, were cultured as described (32).

Immunoblotting

Western blotting analysis was performed as described (8). Briefly, $1.5 \times 10^6$ cells were lysed for 5 min in Laemli buffer (Tris/Hcl pH 6,8, Glycerol 10%, SDS 2%) at 90° C. Tissue samples from control SCID or SCID/mdx mice and from periangioblast-transplanted muscles SCID/mdx mice were homogenized with lysis buffer (50 mM Tris/HCl, pH 7.4, 1 mM EDTA, 1 mM EGTA 1% Triton X-100 and protease inhibitor cocktail (Sigma) and centrifuged at 1000 rpm for 10 min at 4° C. to discard nuclei and cellular debris. The supernatant was separated by SDS PAGE. For western blot analysis, proteins were transferred to Immobilon (Amersham) membranes, saturated with 5% milk, 0.2% TritonX-100 (Sigma) in PBS (blocking solution) and reacted overnight at 4° C. with various antibodies at the appropriate dilution. The filters were washed three times (15 minutes each at RT) with PBS 0.2% TritonX-100 solution and then reacted with anti-mouse secondary antibody conjugated with horse radish peroxidase (HRP) IgG (Biorad) at 1:10000 dilution for 1 hour at RT, washed three times and finally visualized with the ECL immunoblotting detection system (Amersham).

Immunofluorescence

Human periangioblasts were grown on matrigel coated glass coverslips, washed with PBS and fixed with 4% paraformaldehyde for 10 minutes. Muscle samples from control SCID/mdx, or periangioblast-transplanted mdx/SCID mice were frozen in liquid nitrogen cooled isopentane and serial 8 μm thick sections were cut with a Leyca cryostat. Cells were permeabilized with 0.2% Triton X-100, 1% BSA in PBS for 30 minutes at RT, while tissue sections were incubated without detergent. Cells and tissue sections were incubated with 10% donkey serum for 30 min a RT, and incubated overnight at 4° C. with primary antibodies at the appropriate dilution. After incubation, samples were washed two times with the permeabilization buffer and then incubated with the appropriate FITC or TRTC conjugated anti mouse or anti-rabbit IgG and Hoechst for 45 minutes at RT. After three final washes, the cover slips were mounted on glass slides using mowiol in PBS and analyzed under a fluorescent microscope (Nikon). Other tissue sections or cells were stained with X-Gal as described (8).

Antibodies

The following antibodies were used in this study: anti-dystrophin monoclonal antibody Dys1, Dys2 and Dys3 (Novocastra, NCL-Dys1, Dys2 and Dys3) at 1:125 dilution; anti laminin monoclonal or polyclonal antibodies (Sigma L8271 and L9393) at 1:100 dilution; MF20 antibody at 1:5 dilution, anti Smooth Alpha actin 1:300 dilution and anti desmin at 1:50 from Sigma, anti Myf5 1:200 (from Santa Cruz SC302), Pax7 from hybridoma bank at 1:3 dilution, human lam A/C (from Novocastra,NLC-lam/AC) NG2 at 1:250 (a gift from William Stallcup), anti PDGF receptor beta at 1:500 (from Cell Signaling Technologies 56874). For FACS analysis the following antibodies were used CD44, CD34, CD45, CD49b, CD117, CD62L from BD Biosciences (553133, 555821, 555483, 555498, 555714, 555544), CD31, CD13, CD106 from ID labs inc, Cd146 from Biocytes (IDAC 1400, IDAC 1071, IDAC 1272).

Intra-artery Delivery of Periangioblasts

Approximately $5 \times 10^5$ human periangioblasts were injected into mdx/SCID dystrophic mice (from Charles River). Mice were anesthetized with an intraperitoneal injection of physiologic saline (10 ml/kg) containing ketamine (5 mg/ml) and xylazine (1 mg/ml) and a limited incision on the medial side of the leg was performed. Cells were injected via a 0.20-mm-diameter needle inserted into the femoral artery. The needle was connected to a peristaltic pump by a heparinated Tygon tube (Ika Labortechnik). This Tygon tube was connected to a sterile Eppendorf tube containing $1.6 \times 10^6$ cells in 200 μl. Cells were delivered by laminar flow (5 μs) over a period of 10 s. The blood flow was not stopped before or during this procedure. There was no visible damage to the vessel wall during or after operation. The body wall muscle was closed with sutures and the skin with surgical staples. Animals were sacrificed at different times after the injection. Usually, three consecutive injections at 30 days interval were performed Gene Expression Profiling and Data Analysis Total cellular RNA was isolated from human periangioblasts cell populations using RNeasy RNA isolation kit (Qiagen, Valencia, Calif.) following manufacturer's recommendations. Disposable RNA chips (Agilent RNA 6000 Nano LabChip kit) were used to determine the concentration and purity/integrity of RNA samples using Agilent 2100 bioanalyzer. cDNA synthesis, biotin-labeled target synthesis, HG-U133 plus 2.0 GeneChip (Affymetrix, Santa Clara, Calif.) arrays hybridization, staining and scanning were performed according to the standard protocol supplied by Affymetrix. The amount of a transcript mRNA (signal) was determined by the Affymetrix GeneChip Operative Software (GCOS) 1.2 absolute analysis algorithm as already described (33). All expression values for the genes in the GCOS absolute analyses were determined using the global scaling option. Alternatively, probe level data were converted to expression values using robust multi-array average (RMA) procedure (34). Perfect Match (PM) values were background adjusted, normalized using invariant set normalization, and log transformed. The RMA generated data were uploaded onto GeneSpring™ software version 7.2 using the log2 transformation procedure. A "per chip" and a "per gene" normalization were achieved by dividing each signal for the 50.0th percentile of all above-10 signals in that sample and by the median of its values in all samples. A low-level filter in GeneSpring™ filtered out all those probe sets called "Present" in less than 10% of samples or whose normalized expression levels were always between 0.5 and 2 across all of the samples. For supervises analyses an initial filtering procedure was applied in order to select transcripts showing a change call "I" or "D" in at least the 90% of the pair wise comparisons performed using the GCOS comparison algorithm (33). Then, supervised analyses were performed using an ANOVA test (t-test at a confidence level of 0.005) with the Bonferroni correction of the family-wise error rate and using the Significance Analysis of Microarrays (SAM) analysis implemented in the Bioconductor SAM package. The GeneSpring advanced filtering options were used to combine gene lists generated from different analyses. Hierarchical agglomerative clustering was performed in GeneSpring™ using Pearson's correlation coefficient and average-linkage as distance and linkage methods.

Results

Isolation and in vitro Expansion of Cells from Primary Skeletal Muscle Biopsies

A fragment of biopsies of skeletal muscle was obtained, after informed consent, by patients undergoing biopsy for diagnostic purposes and had later been diagnosed either as normal or affected by Duchenne Muscular Dystrophy. Under a dissecting microscope, fragments of vessels and surrounding mesenchymal tissue were dissected and plated on collagen coated dish as previously described for mouse mesoangioblasts (8, 9). After the initial outgrowth of fibroblast-like cells, small round and refractile cells appeared (FIG. 1A) that adhered poorly to the substratum and were thus collected by gently pipetting. Floating cells were either grown as a polyclonal population. After various attempts, an optimal culture medium was devised that supports proliferation of outgrown human periangioblasts. The medium comprises MegaCell® base supplemented with fetal calf serum and bFGF (FIG. 2 and 3). Under these conditions the large majority of the cell population, acquired a triangular, refractile morphology (FIG. 1B) and maintained a high proliferation rate for approximately 20 passages with a doubling time of approximately 36 hrs. (FIG. 1D). Proliferation rate was largely independent from the age of donor (ranging from 20 to 78 years) in the case of normal cells. In cells from DMD patients that derived from children (ranging from 3 to 8 years) the proliferation rate was similar to normal cells (FIG. 1D). This proliferation rate leads to a final number of approximately $10^9$ cells, starting from 5-10.000 cells outgrown. This number of cells would be suitable for intra-arterial delivery to a young patient, based on a per kg comparison with mouse cells delivered to dystrophic mice (8). After 20 passages (approximately 25 PD), large flat cells appeared at increasing frequency. These cells did not divide any more and after few more passages the whole population underwent senescence. At both early and late passages, normal human periangioblasts cells maintained a diploid kariotype (FIG. 1C). When tested for telomerase activity, human normal periangioblasts showed a significant TRAP activity at early (VIII°) passage, approximately 5-10% that found in H1299 reference cancer cells (FIG. 1E). However, at later passages, activity was no longer detected, thus explaining the occurrence of proliferative senescence. Consistently, telomere length progressively shortened and by passage IX° has reached a size typical of pre-senescent cells (FIG. 1F). The same was true for periangioblasts isolated from DMD patients. To test for tumorigenicity, $10^7$ human periangioblasts were injected subcutaneously into nude and SCID mice. 20 injected mice (10 for each group) were maintained up to 12 months after the injection and none of them developed any visible tumor that could be detected macroscopically at autopsy. Human DMD periangioblasts showed identical morphology and culture behavior (karyotype, tumorigenity) but they showed a higher proliferation rate (FIG. 1D), likely linked to the donor age.

Phenotype of Human Periangioblasts

A genome wide analysis on Affimetrix chips of two populations of periangioblasts from normal individuals (and two clones from one of these) and two populations from Duchenne patients revealed that both normal and DMD cells express pericyte markers (10) as follow:
  at high level: annexin V, alkaline phosphatase, desmin, smooth alpha actin, vimentin,
  at medium level: PDGF receptor beta, angiopoietin and NG2 proteoglycan.

By contrast, they do not express myogenic factors, Pax3, Pax7, MEF2C and MEF2D (although they express at low level MEF2A and B), cytokeratins or neurofilaments (with the exception of nestin). Immunocytochemistry and western blot analysis on cultured cells confirmed these results. Much as their mouse counterparts, approximately 10% of both normal and DMD population expressed smooth alpha actin (SMA) and desmin, probably revealing a spontaneous differentiation towards smooth muscle (FIGS. 4a,b). Clones also expressed these markers in the same percentage that did not vary at successive passages. This suggests that smooth muscle cells are continuously generated in culture, but because of a slower proliferation rate, they remain a small fraction of the total cell population. Both normal and DMD human periangioblasts also express PDGF receptor beta at low levels on their surface (with few brightly positive and some negative, FIG. 4c). A high magnification of a cell expressing the receptor (green) on the surface and smooth APha actin (red) is also shown in FIGS. 4d and e. Western blot analysis (FIG. 4h) on extracts of the two normal and two DMD populations of human periangioblasts revealed expression of both the NG2 proteoglycan and of the PDGF receptor beta. The same populations do not express MyoD, Myf5, Myogenin or Pax7 and thus are clearly distinct from satellite cells (FIG. 4g and FIG. 7). In addition, both normal and DMD human periangioblasts express alkaline phosphatase (AP) as shown in FIG. 4K for normal human periangioblasts. Notably, the small, round cells that outgrow from the primary explant, also express AP (inset in FIG. 4K). Since in adult skeletal muscle only pericytes are positive for AP, this observation strongly suggests that human periangioblasts are comprised within the pericyte population. AP distinguishes adult from fetal mouse mesoangioblasts (unpublished observation). To test whether periangioblasts derive from the AP positive population, a biopsy of human normal skeletal muscle was enzymatically digested with 0.1% collagenase (from Sigma C9263)×30 min at 37° C. to a single cell population that was then separated by a fluorescence activated cell sorter into an AP positive and an AP negative fraction. Both populations were then cloned and the number of periangioblasts clones evaluated after 2 weeks. The result of this experiment showed that although AP+ cells represented approximately 10% of the total mono-nucleated cell population, they gave rise to 10 times more clones than the AP− fraction, indicating an enrichment of clonogenic cells of about 100 times in the AP+ fraction (FIG. 4M). Human normal and DMD periangioblasts were also characterized for the expression of surface antigens. The cells were uniformly negative for CD31, CD34, CD45, CD62L, CD106, CD1 17, CD133; they were positive for CD146 and CD49b and strongly positive for CD13 and CD44 (FIG. 4I and FIG. 5). All these results were in agreement with data from microarray analysis. The homogeneity in the expression of these markers revealed that the culture conditions had selected a homogeneous population, at least for the expression of the above antigens. The only striking difference between human and mouse periangioblasts appeared to be the expression of CD34, present in all mouse periangioblasts and absent from the corresponding human cells.

Periangioblasts from DMD patients were indistinguishable from wild type cells for all of the parameters described above, except that for the proliferation rate (see above). The molecular phenotype of human mesoangioblasts from DMD (lanes 1,2 of FIG. 4j) and normal (lanes 3-6) muscle, carried out on Affimetrix chips appeared to be significantly similar, with only few genes differentially expressed: these turned out to be mainly inflammatory genes that appeared to be upregulated in DMD cells, suggesting that even after 10 PD, cells retained in culture the memory of exposure to inflammatory cells and molecules; on the other hand, a few genes such Ephrin B2, Wnt-induced protein 1 and alpha tropomyosin were more expressed in normal cells, but the significance of this is unclear (FIG. 4j and FIG. 6). These genes are mainly inflammatory genes that appeared to be upregulated in DMD periangioblasts, suggesting that cells retained in culture the memory of exposure to inflammatory cells and molecules; on the other hand, very few genes such as Ephrin B2, Wnt-induced protein 1 and alpha tropomyosin were more expressed in normal cells, but the significance of this is unclear. Notably two periangioblasts polyclonal populations (FIG. 4*j* lanes 3,4) and two clones from one of them (FIG. 4*j* lanes 5,6) all express similar profiles, further demonstrating the homogeneity of the cell population selected by the explant culture method.

Differentiation Potency of Human Periangioblasts

To complete the in vitro characterization of normal and DMD human periangioblasts, their ability to undergo terminal differentiation into different mesoderm cell types was tested. Much as their mouse counterparts, human periangioblasts readily differentiate into smooth muscle, osteoblasts or adipocytes when treated with transforming growth factor beta (TGFβ), insulin-dexamethazone or bone morphogenetic protein 2 (BMP2).

In vivo Studies of Human Periangioblasts

The authors then tested the myogenic potency of human periangioblasts in the mdx, immunodeficient mouse. To this aim the authors first evaluated the ability of human periangioblasts to home into downstream skeletal muscles when injected into the femoral artery. To obtain a quantitative measurement, human and murine periangiobalsts were transduced with a lentivector expressing GFP (both populations were over 90% transduced by the vector) and then injected into the femoral artery of mdx/SCID dystrophic mice that do not reject human cells as detailed for mouse cells in Galvez et al. 2006). After 6 hours, mice were sacrificed and individual muscles were dissected from injected and contra-lateral legs as well as filter organs such as liver and spleen. Quantitative PCR for GFP allowed an accurate analysis which revealed that approximately 10% of injected cells home into downstream muscles, less than 1% into contra-lateral muscles, the remaining cells being localized mainly in filter organs (FIG. 8A). The figure shows that human cells were slightly more efficient in homing to skeletal muscle than their mouse counterparts even though the difference was not statistically significant.

The authors next evaluated by immunofluorescence the distribution of human transplanted cells and the subsequent appearance of human dystrophin. After the injection, human nuclei (arrows) were identified (by the anti-human lamin A/C antibody) underneath the basal lamina indicating that at least part of injected cells localize within the muscle fibers as either myonuclei or satellite cells (arrows) in FIG. 8B). Also a group of human cells localized in between and sometimes inside muscle fibers that consequently express human dystrophin can be visualized at low magnification as revealed by staining with anti-human specific antibody Dys3 (FIG. 8C). After three consecutive injections of human cells, large areas of the injected muscle were reconstituted with fibers expressing human dystrophin (FIGS. 8D,E). When dystrophic human periangioblasts, transduced in vitro with a lentiviral vector expressing the human mini-dystrophin were injected into skeletal muscle of mdx/SCID mice, the results were similar to what observed with normal periangioblasts (FIGS. 8F,G). The amount of human dystrophin expressed in transplanted muscles was analyzed by Western Blot (FIG. 8H) and revealed significant accumulation of both wild type and mini-dystrophin, although with differences among different transplanted animals.

Discussion

Isolation and Characterization of Human Periangioblasts

The data reported in this invention show that it is possible to isolate periangioblasts from biopsies of skeletal muscle from both healthy subjects and dystrophic patients. The cells can be expanded in vitro for about 20 passages (roughly 40 population doublings), transduced with viral vectors and then induced to differentiate into skeletal muscle. When transplanted into dystrophic immune-incompetent mice, such periangioblasts give rise to large numbers of new fibers expressing human dystrophin. Therefore this human cell population fulfils all the criteria required for a successful cell therapy protocol in muscular dystrophies.

Moreover the authors show in the present invention that periangioblasts express alkaline phopshatase and a number of pericyte markers and indeed derive from cells that in vivo also express AP, i.e. pericytes (11). Therefore it is concluded that human and mouse periangioblasts are comprised within the pericyte population and occupy a perithelial position in vivo. They do not express endothelial markers, contrary to embryonic mesoangioblasts that transiently express Flk1, Tie2 and CD31 when isolated from embryonic vessels.

Normal and DMD periangioblasts can be easily isolated from the same biopsy that is used for diagnosis, with no need for additional surgical intervention. In any case a needle biopsy is a tolerable surgery that could be repeated every few years. The source of cells is important not only for practical reasons. It is possible that these multipotent mesoderm progenitors, receive some sort of local commitment that favors recruitment into the cell types of the tissue where they reside. As a matter of fact, the percentage of human periangioblasts nuclei that are incorporated into hybrid myotubes, after co-culture with mouse myoblasts, is strikingly high, ranging from 30 to 60% in different experiments. This is significantly more than what observed with other types of stem cells derived from non-muscle sources.

Moreover, the present invention demonstrates that human normal and DMD periangioblasts differentiate spontaneously into skeletal myotubes (up to 40% of the population) upon appropriate culture conditions. This is a striking difference with mouse mesoangioblasts that could only be induced to differentiate by co-culture with myoblasts (8, 9). This characteristic may result in a dramatic therapeutic improvement with increased efficiency of reconstitution of large muscles in muscular dystrophic patients.

A Comparison with Other Stem Cells of the Mesoderm

Because of their origin, the authors first considered the possibility that human periangioblasts may represent a different subset of mesenchymal stem cells (MSC) that also originate from the pericytes of bone marrow (13). However, a detailed comparison of human periangioblasts with mesenchymal stem cells showed that the two cell populations clearly differ in the expression of a significant number of genes. More importantly, human mesoangioblasts do not grow in a-MEM, the medium used for MSC, thus confirming that these populations are indeed distinct.

In the last several years many different types of mesoderm stem cells have been isolated from both mouse and human tissues and characterized to different extent. These include endothelial progenitor cells (EPC, 14), multipotent adult progenitor cells (MAPC, 15), muscle derived stem cells (MDCS, 16), side population cells (SP, 17-19), mesoangioblasts (9), stem/progenitor cells from muscle endothelium (20), sinovia (21) dermis (22), and adipose tissue (23). Different experimental procedures, different sources and partial characterization still prevent a complete understanding of the heterogeneity of these cells; even less is known on their origin and possible lineage relationships. Many of these cells, such as MDSC or MAPC have been shown to differentiate into skeletal muscle in vitro and for MDSC also after transplantation into dystrophic muscle. However, human MDSC have not yet been isolated. Some of these cells grow extensively in vitro but others such as EPC and SP do not; on the other hand EPC and SP can be delivered in the blood whereas systemic delivery has not been tested for most of the other cell types.

Currently, human periangioblasts of the present invention are the only cell type for which all the requested criteria have been validated, although it is possible that other mesoderm cell types may also show similar features.

For example, it was recently shown that cells isolated from adipose tissue can be extensively grown in vitro, differentiate into several tissues including skeletal muscle and give rise to human dystrophin-expressing fibers when injected into mdx mice, even in the absence of immune suppression (23). Such a surprising result awaits confirmation, since stem cells may escape the immune system (24) but the fibers they form express high levels of class I HLA antigens (25). Moreover, a biochemical analysis of the amount of dystrophin produced was not reported, making a direct comparison with the present invention difficult. Finally, MSC that usually differentiate into skeletal muscle with low efficiency, were reported to give rise to numerous fibers in vitro and in mdx muscle when transduced with the intracellular active domain of Notch and exposed to certain cytokines (26). This paradoxical result is intriguing and awaits for a molecular explanation. Indeed Notch is known as a myogenesis inhibitor (27) having transforming ability (28).

Perspectives for a Clinical Trial with Periangioblasts

In clinical protocols, systemic delivery appears as an obligate choice, since intra-muscular delivery would require numberless injections. Human and mouse periangioblasts express some of the proteins that leukocytes use to adhere to and cross the endothelium (e.g. vascular cell adhesion molecule (VCAM-1), inducible cell adhesion molecule (ICAM-1/5/2), leukocyte selectin (L-Selectin), CD36, CD44, b7, b5, b1, b2 integrins, a integrins (a1, a5 and a6), leukocyte factor antigen (LFA-1), interleukin-1 receptor IL-1R, stromal derived factor receptor (SDF-R) and cadherins) and thus can diffuse into the interstitium of skeletal muscle when delivered intra-arterially. This is a distinct advantage over resident satellite cells that cannot do the same; it is likely that other mesoderm stem/progenitor cells will show the same ability but this has not been tested so far. Moreover, the authors have recently shown that transient expression of α-4 integrin or L-selectin in mouse periangioblasts, previously exposed to Sdf-1 (stromal cell-derived factoror-1) or TNF-α, increases by four to five fold their homing to skeletal muscle (42), a simple procedure that may further increase the colonization of patients muscle by donor cells. Catheter mediated delivery to the succlavia, the diaphragmatic or the iliac arteries should allow periangioblasts to reach and colonize muscles essential for motility and breathing.

An additional concern for cell therapy protocols is the risk that extensive expansion in vitro may compromise differentiation and/or self-renewal ability or even lead to malignant transformation. The present invention demonstrates that human periangioblasts can be grown extensively but not indefinitely in vitro. Importantly, human dystrophic periangioblasts show the same proliferation ability as their normal counterparts, suggesting that the disease has not exhausted their growth potency, at least in young age. Both normal and dystrophic periangioblasts maintain a diploid karyotype, are not tumorigenic in immune deficient mice and undergo senescence after approximately 20 passages in vitro. It should be considered that periangioblasts mainly give rise to terminally differentiated, post-mitotic and long lasting muscle fibers. Should the case, a new batch of cells could be easily obtained with a second needle biopsy. Finally, two protocols appear now as alternative choices for cell therapy of dystrophy: a) autologous dystrophic cells after gene correction in vitro or b) normal donor cells in the presence of immune suppression. In the case of muscular dystrophy, gene correction of autologous cells faces the problem represented by the huge size of dystrophin; the authors show here that expression of human mini-dystrophin from lentiviral vectors efficiently restore dystrophin synthesis, even though lentiviral vectors are not yet approved for use in patients and, functional efficacy of the modified dystrophin remains to be tested in the context of a large muscle fiber.

Donor cell transplantation would overcome these problems but faces the need for a life long immune suppression that would also start early in life.

In conclusion the authors have shown that human periangioblasts are an ideal cell population for cell therapy of muscular dystrophy. As a matter of fact, experiments in the Golden Retriever Muscular Dystrophy indicate that functional amelioration of dystrophic dogs is possible (43) and suggest therapeutic applications of cells of the present invention.

Cardia Mesoangioblasts

Methods
Isolation and Culture of Mouse and Human Cardiac Mesoangioblasts

Hearts isolated from 4 weeks old HomoGFP mice (from Charles River) were kept in DMEM (Sigma, D5671) without FCS, with antibiotics (Penicillin/Streptomycin) and subdivided in five different regions: aorta, ventricle, auricle, free wall and septum. Each piece was rinsed in PBS with Ca/Mg and sharply dissected into 1-2 mm diameter pieces with a scalpel. Fragments containing small vessels were transferred to a Petri dish coated with gelatin 1% (Sigma G9382) in presence of 20% FBS-DMEM plus 5 mM glutamine and antibiotics as previously described for mouse mesoangioblasts (8,9). These hearts fragments were cultured for 8-15 days depending on the region and after the initial outgrowth of fibroblast-like cells, small round and retractile cells appeared. This cell population was easily collected by gently pipetting the original culture, counted and cloned by limited dilution on gelatin 1% coated 96 multiwell plates. Different clones were selected by phase contrast morphology, expanded and then characterized by surface markers expression.

Human cardiac mesoangioblasts were isolated from biopsies of patients undergoing surgery for atrial valvular disfunction, essentially as described above for mouse cardiac mesoangioblasts.

Mouse Cardiac Mesoangioblast Differentiation Assays

Differentiation into cardiac cells was induced by co-culturing adult mice cardiac mesoangioblasts clones with rat neonatal cardiomyocytes. Cardiac mesoangioblasts were added at 1:5 ratio and cultures were shifted to differentiation medium (DMEM supplemented with 2% horse serum). After 5 days, cultures were fixed and stained with antibodies against myosin (MF20). Identification of nuclei was confirmed by Hoechst staining. The percentage of cardiac differentiation was calculated by counting the number of green GFP-cardiac mesoangioblasts that were positive for myosin staining (red). Biochemical differentiation was confirmed by RT-PCR using mice specific oligonucleotides for Nkx2.5, GATA4/6, isl-1, mef2a and Tbx2/6 with RNA extracted from the different cardiac mesoangioblasts clones.

Human Cardiac Mesoangioblast Differentiation Assays

Differentiation into cardiac cells was induced either by exposing cells to 5,1M 5-azacytidine or by co-culturing mouse or human cardiac mesoangioblasts with neonatal cardiomyocytes. In order to distinguish between the populations, mouse or rat neonatal cardiomyocytes are utilised.

Mouse Cardiac Muscle Cellular Electrophysiology

Electrophysiological studies on mouse cardiac mesoangioblasts were performed at 35° C. Membrane currents were recorded using the whole cell mode of the patch-clamp technique and the capacitance was also measured (Hamill O P et al., 1981). Data analysis and graphs were obtained with Clampfit 8.1 and Origin version 7.0.

Analysis of Cardiac Muscle Cell Proliferation

Mouse cardiac mesoangioblasts were plated at a density of $5 \times 10^3$ cells/cm$^2$ in different media and passed on average every three days. At each passage, the number of cells was counted in triplicate in a hemocytometer. For the growing curve of the cardiac clones, cells were plated initially at $1 \times 10^4$ cells/cm$^2$ in complete DMEM and passed every five days. At each passage, the number of cells was counted in triplicate in the hemocytometer.

Results

Mouse Cardiac Mesoangioblasts

Isolation and in vitro Expansion of Mouse Cardiac Mesoangioblasts.

Adult heart were collected, dissected and plated as indicated above. After the initial outgrowth of fibroblast-like cells, small round and refractile cells appeared. These cells adhered poorly to the substratum and were thus collected by gently pipetting. Floating cells were cloned by final dilution on gelatin 1% coated plates (without feeder layers).

The medium used in this case for growing and cloning was complete DMEM with 20% serum. Under these conditions some of the clones acquired a triangular, refractile morphology under subclonfluent conditions (FIGS. 9A-E) or cobblestone pattern under confluent condition (FIGS. 9A'-E'), maintaining a medium proliferation rate for approximately 25 passages with a doubling time of approximately 72 h (FIG. 10). Proliferation rate varied with the anatomic origin of the clone: aorta, ventricle and free wall derived clones were faster in growing than those derived from auricle or septum (FIG. 10). This proliferation rate leads to a final number of approximately $1 \times 10^9$ cells, starting from 10.000 cells outgrown in the best of the cases with aorta clone. After 25 passages, large flat cells appeared at increasing frequency. These cells did not divide any more and after few more passages the whole population underwent senescence.

Adult mouse cardiac clones were further characterized by flow cytometry and PCR gene expression (tables I and II and FIG. 11) and their ability for differentiation to cardiomyocytes was analyzed by immunostaining (FIGS. 12, 13 and Table III) and electrophysiology (FIG. 14).

Characterization of Mouse Cardiac Mesoangioblast Surface Markers and Genes Expression Adult cardiac clones from the different heart regions were analyzed by flow cytometry for the expression at the cell surface of stem cells markers. All clones were CD34, CD31, Sca-1, c-kit and CD44 positive and CD45 negative (Table I).

TABLE I

| Surface markers for mouse cardiac mesoangioblasts | | | | | | |
|---|---|---|---|---|---|---|
| | CD45 | CD34 | CD44 | CD31 | Sca-1 | c-kit |
| Aorta E8 | − | + | + | + | + | + |
| Ventricle J2 | − | + | + | + | + | + |

In addition, RNA was extracted from the different mouse adult cardiac clones cells while growing (ND, non differentiated) or after 5 days of differentiation (DIF, differentiated, Table II). RT-PCR was performed for analyzing the expression of different genes involved in cardiac development or differentiated previously described by other groups (Table II and FIG. 11).

TABLE II

| Cardiac genes for mouse cardiac mesoangioblasts | | | | |
|---|---|---|---|---|
| | AORTA ND | AORTA DIF | VENTRIC ND | VENTRIC DIF |
| Isl-1 | + | + | + | + |
| Nkx2.5 | + | + | + | + |
| Gata4 | + | + | + | + |
| Gata6 | + | + | + | + |
| Mef2a | − | − | − | − |
| Mef2c | − | + | − | + |
| Tbx2 | + | + | + | + |
| Tbx5 | + | + | + | + |
| Tbx6 | − | + | − | + |

FIG. 11 shows that clones differed from each other for the expression of cardiac specific transcription factors such as MEF2 and Tbx5.

Differentiation Potency of Mouse Cardiac Mesoangioblasts

Mouse cardiac mesoangioblasts were unable to readily differentiate into smooth muscle, osteoblasts or adipocytes when treated with transforming growth factor beta (TGFβ), insulin-dexamethazone or bone morphogenetic protein 2 (BMP2). In contrast, when cardiac muscle differentiation was induced by co-culture of these adult cardiac clones with rat neonatal cardiomyocytes, higher number of aorta clone cells expressed sarcomeric myosin, showing that these cells have a potent ability to undergo cardiomyogenesis (up to 90%, FIG. 12). Moreover, unexpectedly, when aorta or FW clone cells were exposed to cardiac differentiation medium (low serum), approximately 70-80% of cells spontaneously differentiated into myosin positive cardiomyocytes (FIG. 13). The authors also observed differences depending on the region from where cardiac clones were isolated (Table III).

TABLE III

| Differentiation of mouse cardiac mesoangioblasts | | | | | |
|---|---|---|---|---|---|
| Cell clone | Aorta E8 | Ventricle J2 | Auricle K1 | Free Wall B8 | Septum G3 |
| Spontaneous cardiac differentiation | >90% | >90% | <1% | <1% | <1% |
| Co-culture induced cardiac differentiation | ~90% | ~80% | ~70% | ~20% | ~10% |

Functional Studies of Mouse Cardiac Mesangioblasts

To assess the functional properties of the mouse adult cardiac mesoangioblasts, electrophysiological experiments were carried out at physiological temperature (35-37° C.) on the ventricle cardiac clones cells. FIG. 14A, shows an isolated ventricle cardiac cell beating while making the measurements. The capacitance of these cells is comparable to the ones obtained with fresh isolated mouse cardiomyocytes (134.5+−6.8 pF, n=12) as shown FIG. 14B. Interestingly, when recording action potencials from these cells, the waveforms pattern the authorsre similar to the ones obtained with freshly isolated left ventricular myocytes (FIG. 14C).

Therefore, ventricle cardiac expressed rhythmic contractile activity and appropriate ionic channels. They seems to behave in a similar way as a ventricular cardiomyocyte.

Human Cardiac Mesoangioblasts
Isolation and Characterization of Human Cardiac Mesoangioblast Human cardiac mesoangioblasts were isolated from human ventricle, auricle or aorta biopsies following the protocol detailed in methods. As shown in FIGS. 15(A,B), these cells have a similar morphology to the mice cardiac mesoangioblast and were able to grow in presence of different mediums at a high rate (FIG. 15C).

Human cardiac mesoangioblasts expressed CD31, CD44, CD34 and CD117 but did not express CD45 nor CD133 (Table IV).

TABLE IV

Surface marker in human cardiac mesoangioblasts

|  | CD31 | CD34 | CD44 | CD45 | CD117 | CD133 |
|---|---|---|---|---|---|---|
| Ventricle | + | + | + | − | + | − |
| Aorta | + | + | + | − | + | − |
| Auricle | + | + | + | − | + | − |

The authors also studied the gene expression pattern of these cells (Table V)

TABLE V

Cardiac genes for human cardiac mesoangioblasts

|  | Nkx2.5 | Isl-1 | Gata4 | Mef2A | Tbx2 | Tbx5 |
|---|---|---|---|---|---|---|
| Ventricle | + | − | + | + | + | + |
| Aorta | + | − | + | + | + | + |
| Auricle | + | − | + | + | + | + |

Human cardiac mesoangioblasts were positive for nkx2.5, gata4, tbx2/5 and mef2A but negative for isl1.

Differentiation Potency of Human Cardiac Mesoangioblast

Cardiac muscle differentiation was induced by co-culture with rat neonatal cardiomyocytes: up to 35% of the human cells differentiated and expressed cardiac actin (Table VI). Moreover, these cells can differentiate into cardiomyocytes in presence of 5-azacytidine (5 µM) (FIG. 16 and Table VI).

TABLE VI

Differentiation rate for human cardiac mesoangioblasts

| % | 5-aza | Co-culture | Spontaneous |
|---|---|---|---|
| Ventricle | 55 | 35 | no |
| Aorta | 35 | 19 | no |
| Auricle | 21 | 12 | no |

Discussion
Mouse Cardiac Mesoangioblasts

In the present invention, the authors show that it is possible to isolate cardiac mesoangioblast-like stem cells from different regions of the adult mouse heart. Previously, it has been reported by Anversa or Chien the possibility of obtaining stem cells from adult heart but the goal of this work is to obtain distinct cardiac stem cells from the different region of the heart with different differentiation and functional properties. The authors isolated cardiac mesoangioblasts from the aorta, ventricle, auricle, free wall and septum that can grow until 25 passages and express stem cells surface markers like Sca-1 or c-kit and cardiac genes like nkx2.5 or gata4. A comparative analysis of marker expression in different cardiac stem/progenitor cells is shown below in Table VII:

TABLE VII

| Marker | CPC Schneider | ACSC Anversa | Cardioblasts Chien | Mouse Cardiac Cossu |
|---|---|---|---|---|
| CD45 | − | − | − | − |
| CD31 | − | − | ? | + |
| CD34 | − | − | − | + |
| Sca-1 | + | + | + | + |
| c-Kit | − | + | + | + |
| GATA4 | + | + | + | + |
| Nkx2.5 | − | + | ? | + |
| MEF2C | + | + | ? | − |
| Isl-1 | ? | ? | + | + |

Besides, these mouse adult cardiac mesoangioblasts are not only able to differentiate in co-culture with cardiomyocytes but also in presence of diffentiated medium (low serum). They can express sarcomeric myosin together with several cardiac markers as show in upper tables (Tables I and II). By electrophysiological approaches the authors showed that these adult cardiac cells have functional channels for the current and behave similar to ventricular myocytes. Thus the authors have a potent tool for studying the cardiac differentiation mechanisms and for therapeutical applications of cardiac diseases.

Human Cardiac Mesoangioblasts

The present invention demonstrates the possibility of isolating human cardiac stem cells from explants from human adult biopsies, not only from the auricle but also from the ventricle or aorta region. Cells can be grown and expanded in vitro. They have the ability to differentiate into cardiomyocytes in vitro when co-cultured with rat neonatal cardiomyocytes. Their electrical properties still remained unknown as well as their ability to differentiate in vivo. Human cardiac mesoangioblasts, as shown in above tables (Tables IV and V), express all surface markers and cardiac genes necessary for the cardiac commitment similarly to the mouse cardiac mesoangioblasts. This makes them suitable for therapy in human patients affected by cardiac disorders.

Perspectives for a Clinical Trial with Cardiac Mesoangioblasts

Until now, the use of embryonic stem cells as tool for cell therapy in the heart has been limited by possible tumorigenity and the need for immune suppression, although these cells are highly efficient in generating functional cardiomyocytes (44-46). The discovery of cardiac mesoangioblasts in adult heart with high cardiomyogenic potential opens a new possibility for the treatment of human patients. Colonization of the ventricle wall by these cells and their subsequent differentiation into cardiomyocytes in vivo has been demonstrated by electron microcopy and histology. This results in a significant but not complete functional recovery. Interestingly, cardiac mesoangioblasts do not appear able to migrate inside the necrotic area for more than a few mm. Coronary artery ligation results in a large trans-mural infarction, and cells may not be able to heal the whole area unless neo-angiogenesis and/or removal of necrotic tissues allows successive migration. In pathologies like muscular dystrophies, where areas of necrosis are inter-dispersed with regenerating or apparently healthy areas, mesoangioblast transplantation results in highly efficient tissue repair (43). Thus other cardiac diseases not resulting in massive necrosis of cardiac tissues, such as hypertrophy may be better targets for cell therapy with cardiac mesoangioblasts.

The isolation method for cardiac mesoangioblasts from adult mice hearts of the present invention has already been used for the isolation of their counterpart in human, favoring the generation of committed human cardiac progenitors that can be used in autologous therapies.

REFERENCES

1. Mauro, A. 1961. *J. Biophys. Biochem. Cytol.* 9:493-495.
2. Sherwood, R. I., et al. 2004. *Cell.* 12:543-554.
3. Collins, C. A., et al. 2005. *Cell.* 29:289-301.
4. Beauchamp, J. R., et al. 1999. *J. Cell Biol.* 144:1113-1121
5. Montarras, D., et al. 2005. *Science.* 23:2064-2067. Epub 2005 Sep. 1.
6. Skuk, D. and Tremblay, J. P. 2003. *J. Muscle. Res. Cell. Motil.* 24:285-300.
7. Cossu, G. and Sampaolesi, M. 2004. *Trends Mol. Med.* 10: 516-520
8. Sampaolesi M, et al. 2003. *Science.* 301:487-492.
9. Minasi, M. G., et al. 2002. *Development* 129, 2773-2783.
10. Armulik, A., Abramsson, A., and Betsholtz, C. 2005. *Circ. Res.* 97:512-523.
11. Safadi, A., et al. 1991. *J. Histochem. Cytochem.* 39:199-203.
12. 
13. Bianco, P. and Gehron Robey, P. 2000. *J. Clin. Invest.* 105:1663-8.
14. Asahara, T. et al. 1997. *Science* 275:964-967.
15. Reyes, M., et al. 2001. *Blood* 98:2615-2625.
16. Qu-Petersen, Z., et al. 2002. *J. Cell Biol.* 157: 851-864.
17. Asakura, A., et al. 2002. *J. Cell Biol.* 159:123-134.
18. LaBarge, M. A., and Blau, H. M. 2002. *Cell* 111:589-601.
19. Bachrach, E., et al. 2004. *Proc. Natl. Acad. Sci.* 9:3581-3586.
20. Tamaki. T., et al. 2002. *J. Cell Biol.* 157: 571-577.
21. De Bari, C., et al. 2003. *J. Cell Biol.* 17:909-918. Epub Mar. 10, 2003.
22. Toma, J. G., et al. 2001. *Nat. Cell. Biol.* 3:778-784.
23. Rodriguez, A. M., et al. 2005. *J. Exp. Med.* 2:1397-1405.
24. Krampera, M., et al. 2003. *Blood.* 101:3722-3729
25. Pavlath, G. K. 2002. *J. Neuroimmunol.* 125:42-50
26. Dezawa, M., et al. 2005. *Science.* 8:314-317.
27. Luo, D., Renault, V. M., and Rando, T. A. 2005. *Cell. Dev. Biol.* 16:612-622
28. Leong, K. G., and Karsan, A. 2005. *Blood.* [Epub ahead of print]
29. Wright, W. E., Shay, J. W., and Piatyszek, M. A. 1995. *Nucleic. Acids. Res.* 23:3794-4005.
30. Ouellette, M. M., et al. 2000. *J. Biol. Chem.* 7:10072-10076.
31. Li, S., et al. 2005. *Gene. Ther.* 12:1099-1108.
32. Lattanzi, L., et al. 1998. *J. Clin. Invest.* 15:2119-2128.
33. Irizarry, R. A., et al. 2003. *Biostatistics.* 4: 249-264.
34. Liu, W. M., et al., 2002. *Bioinformatics.* 18:1593-1599.
35. Olson, E. (2004). Nat Med 10, 467-474.
36. Beltrami, A., et al. (2003). Cell 114, 763-776.
37. Oh, H., et al. (2003). PNAS 100, 12313-12318.
38. Laugwitz, K., et al. (2005). Nature 433, 647-653.
39. Messina, E., et al. (2004). Circ Res 95, 911-921.
40. Kocher, A., et al., (2001). Nat Med 7, 430-436.
41. Galli, R., et aL (2001). PNAS 98, 10733-10738.
42. Galvez, B., et al., (2006). J Cell Biol 174, 231-243.
43. Sampaolesi M, et al. (2006). Nature 444, 574-579.
44. Kehat, I., et al., (2001). J Clin Invest 108, 407-414.
45. Menard, C., et al. (2005). Lancet 366, 1005-1012.
46. Kolossov, E., et al. (2006). J Exp Med.

The invention claimed is:

1. An isolated skeletal muscle periangioblast cell population expressing the following marker phenotype: $CD31^-$, $CD34^-$, $CD45^-$, $CD62L^-$, $CD106^-$, $CD117^-$, $CD133^-$, $CD146^+$, $CD49b^+$, $CD13^+$ and $CD44^+$.

2. The isolated skeletal muscle periangioblast cell population according claim 1 being able to spontaneously differentiate in vitro in the myogenic lineage in suitable culture conditions.

3. An in vitro method for isolating a skeletal muscle periangioblast cell population according to claim 1 from a human skeletal muscle tissue sample, comprising the steps of: a) allowing dissociation of cells from the skeletal muscle tissue sample by non proteolytic digestion means; b) culturing dissociated cells in a mammalian cell growth medium including growth factors, amino acids, trace elements, non essential amino acids, fetal calf serum and Fibroblast Growth Factor-beta.

4. The in vitro method of claim 3, wherein the growth medium is the MegaCell DMEM or the Iscov medium.

5. The in vitro method of claim 4 further comprising the step of incubating cultured extracted cells with stromal cell-derived factor-1 or Tumor Necrosis factor-alpha.

6. The in vitro method of claim 3 wherein the donor is affected by muscular dystrophy.

7. The in vitro method of claim 6 wherein the muscular dystrophy is Duchenne muscular dystrophy.

* * * * *